United States Patent
Visvanathan et al.

(10) Patent No.: US 10,507,241 B2
(45) Date of Patent: Dec. 17, 2019

(54) BIOMARKERS USEFUL IN THE TREATMENT OF IL-23A RELATED DISEASES

(71) Applicant: BOEHRINGER INGELHEIM INTERNATIONAL GMBH, Ingelheim am Rhein (DE)

(72) Inventors: Sudha Visvanathan, Ridgefield, CT (US); Patrick Baum, Ingelheim am Rhein (DE); Oliver Kleiner, Ingelheim am Rhein (DE); Ulrich Kunz, Ingelheim am Rhein (DE)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 0 days.

(21) Appl. No.: 15/327,144

(22) PCT Filed: Jul. 23, 2015

(86) PCT No.: PCT/US2015/041706
§ 371 (c)(1),
(2) Date: Jan. 18, 2017

(87) PCT Pub. No.: WO2016/014775
PCT Pub. Date: Jan. 28, 2016

(65) Prior Publication Data
US 2017/0157246 A1    Jun. 8, 2017

Related U.S. Application Data

(60) Provisional application No. 62/028,379, filed on Jul. 24, 2014.

(51) Int. Cl.
*C12Q 1/6883* (2018.01)
*A61K 39/395* (2006.01)
(Continued)

(52) U.S. Cl.
CPC ........ *A61K 39/3955* (2013.01); *C12Q 1/6883* (2013.01); *G01N 33/53* (2013.01);
(Continued)

(58) Field of Classification Search
None
See application file for complete search history.

(56) References Cited

U.S. PATENT DOCUMENTS

| 6,060,284 A | 5/2000 | Bazan |
| 6,479,634 B1 | 11/2002 | Bazan |

(Continued)

FOREIGN PATENT DOCUMENTS

| EP | 1 072 610 A1 | 1/2001 |
| EP | 2 786 746 A1 | 10/2014 |

(Continued)

OTHER PUBLICATIONS

Sofen et al. Guselkumab (an IL-23—specific mAb) demonstrates clinical and molecular response in patients with moderate-to-severe psoriasis. J Allergy Clin Immunol. Apr. 2014;133(4):1032-40.*
(Continued)

*Primary Examiner* — Diana B Johannsen
(74) *Attorney, Agent, or Firm* — Foley & Lardner LLP

(57) ABSTRACT

This invention generally relates to biomarkers useful in the treatment of IL-23 related diseases, in particular inflammatory diseases such as psoriasis. The invention also relates to methods of using the biomarkers disclosed herein, for example in therapies utilizing IL-23 antagonists.

10 Claims, 4 Drawing Sheets

Specification includes a Sequence Listing.

(51) Int. Cl.
  *G01N 33/68*     (2006.01)
  *G01N 33/53*     (2006.01)
(52) U.S. Cl.
  CPC ..... *G01N 33/5308* (2013.01); *G01N 33/6863* (2013.01); *G01N 33/6869* (2013.01); *A61K 2121/00* (2013.01); *C12Q 2600/106* (2013.01); *C12Q 2600/158* (2013.01)

(56) References Cited

U.S. PATENT DOCUMENTS

| | | |
|---|---|---|
| 6,495,667 B1 | 12/2002 | Bazan |
| 6,610,285 B1 | 8/2003 | Hirata |
| 6,756,481 B2 | 6/2004 | Chirica et al. |
| 6,835,825 B1 | 12/2004 | Bazan |
| 7,090,847 B1 | 8/2006 | Oppmann et al. |
| 7,183,382 B2 | 2/2007 | Oppmann et al. |
| 7,252,967 B2 | 8/2007 | Hirata |
| 7,282,204 B2 | 10/2007 | Oft et al. |
| 7,332,156 B2 | 2/2008 | Bowman et al. |
| 7,411,041 B2 | 8/2008 | Chirica et al. |
| 7,422,743 B2 | 9/2008 | Chirica et al. |
| 7,427,402 B2 | 9/2008 | Kastelein et al. |
| 7,491,391 B2 | 2/2009 | Benson et al. |
| 7,501,247 B2 | 3/2009 | Kastelein et al. |
| 7,510,709 B2 | 3/2009 | Gurney |
| 7,510,853 B2 | 3/2009 | Chirica et al. |
| 7,575,741 B2 | 8/2009 | Bowman et al. |
| 7,608,690 B2 | 10/2009 | Bazan |
| 7,740,848 B2 | 6/2010 | Kastelein et al. |
| 7,749,718 B2 | 7/2010 | Chirica et al. |
| 7,750,126 B2 | 7/2010 | Hirata |
| 7,754,214 B2 | 7/2010 | Chirica et al. |
| 7,790,862 B2 | 9/2010 | Lewis et al. |
| 7,807,160 B2 | 10/2010 | Presta et al. |
| 7,807,414 B2 | 10/2010 | Benson et al. |
| 7,820,168 B2 | 10/2010 | Cua et al. |
| 7,872,102 B2 | 1/2011 | Beidler et al. |
| 7,883,695 B2 | 2/2011 | Oppmann et al. |
| 7,887,806 B2 | 2/2011 | Chirica et al. |
| 7,893,215 B2 | 2/2011 | Bowman et al. |
| 7,910,703 B2 | 3/2011 | Lewis et al. |
| 7,935,344 B2 | 5/2011 | Benson et al. |
| 7,993,645 B2 | 8/2011 | Benson et al. |
| 8,106,177 B2 | 1/2012 | Benson et al. |
| 8,778,346 B2 | 7/2014 | Barrett et al. |
| 9,441,036 B2 | 9/2016 | Barrett et al. |
| 2004/0219150 A1 | 11/2004 | Cua et al. |
| 2004/0258686 A1 | 12/2004 | Chirica et al. |
| 2005/0039222 A1 | 2/2005 | Habu et al. |
| 2005/0100917 A1 | 5/2005 | Chirica et al. |
| 2005/0100918 A1 | 5/2005 | Chirica et al. |
| 2005/0100965 A1 | 5/2005 | Ghayur et al. |
| 2005/0208052 A1 | 9/2005 | Katsikis et al. |
| 2005/0244874 A1 | 11/2005 | Kastelein et al. |
| 2005/0287593 A1 | 12/2005 | Kastelein et al. |
| 2006/0088523 A1 | 4/2006 | Andya et al. |
| 2006/0140958 A1 | 6/2006 | Hogan et al. |
| 2007/0009526 A1 | 1/2007 | Benson et al. |
| 2007/0218060 A1 | 9/2007 | Long et al. |
| 2008/0199460 A1 | 8/2008 | Cua et al. |
| 2008/0200655 A1 | 8/2008 | Sek |
| 2008/0254026 A1 | 10/2008 | Long et al. |
| 2008/0311043 A1 | 12/2008 | Hoffman et al. |
| 2009/0060906 A1 | 3/2009 | Barry et al. |
| 2009/0092604 A1 | 4/2009 | Cua et al. |
| 2009/0123479 A1 | 5/2009 | Bembridge et al. |
| 2009/0156788 A1 | 6/2009 | Presta et al. |
| 2009/0291062 A1 | 11/2009 | Fraunhofer et al. |
| 2010/0003251 A1 | 1/2010 | Oft et al. |
| 2010/0041144 A1 | 2/2010 | Bazan |
| 2010/0111950 A1 | 5/2010 | Cua et al. |
| 2010/0111954 A1 | 5/2010 | Cua et al. |
| 2010/0111966 A1 | 5/2010 | Presta et al. |
| 2010/0135998 A1 | 6/2010 | Bowman et al. |
| 2010/0143357 A1 | 6/2010 | Cua et al. |
| 2010/0254991 A1 | 10/2010 | Kastelein et al. |
| 2010/0261273 A1 | 10/2010 | Chirica et al. |
| 2010/0266582 A1 | 10/2010 | Gurney |
| 2010/0266583 A1 | 10/2010 | Gurney |
| 2010/0272731 A1 | 10/2010 | Presta et al. |
| 2010/0291084 A1 | 11/2010 | Kopf et al. |
| 2010/0322863 A1 | 12/2010 | Benson et al. |
| 2011/0002942 A1 | 1/2011 | Presta et al. |
| 2011/0059087 A1 | 3/2011 | Lewis et al. |
| 2011/0135597 A1 | 6/2011 | Bowman et al. |
| 2011/0142831 A1 | 6/2011 | Cua et al. |
| 2011/0142853 A1 | 6/2011 | Presta et al. |
| 2011/0159589 A1 | 6/2011 | Lewis et al. |
| 2011/0177022 A1 | 7/2011 | Oppmann et al. |
| 2011/0195455 A1 | 8/2011 | Benson et al. |
| 2011/0206686 A1 | 8/2011 | Bembridge et al. |
| 2011/0212104 A1 | 9/2011 | Beaumont et al. |
| 2011/0229490 A1 | 9/2011 | Li et al. |
| 2011/0250201 A1 | 10/2011 | Smith |
| 2011/0311527 A1 | 12/2011 | Stern et al. |
| 2012/0128689 A1 | 5/2012 | Clarkson et al. |
| 2012/0195885 A1 | 8/2012 | Correia et al. |
| 2012/0277799 A1 | 11/2012 | Winslow et al. |
| 2012/0282269 A1 | 11/2012 | Barrett et al. |
| 2013/0004501 A1 | 1/2013 | Towne et al. |
| 2013/0028907 A1 | 1/2013 | Parshad et al. |
| 2013/0115166 A1 | 5/2013 | Clarke et al. |
| 2013/0216525 A1 | 8/2013 | Chen |
| 2014/0046063 A1 | 2/2014 | Moussy et al. |
| 2014/0178401 A1 | 6/2014 | Nabozny et al. |
| 2014/0303357 A1 | 10/2014 | Lim et al. |
| 2014/0363444 A1 | 12/2014 | Barrett et al. |
| 2016/0060338 A1 | 3/2016 | Barrett et al. |
| 2016/0222102 A1 | 8/2016 | Arndt et al. |
| 2016/0333091 A1 | 11/2016 | Barrett et al. |
| 2017/0022294 A1 | 1/2017 | Singh et al. |

FOREIGN PATENT DOCUMENTS

| | | |
|---|---|---|
| WO | WO-99/05280 A1 | 2/1999 |
| WO | WO-99/40195 A1 | 8/1999 |
| WO | WO-99/54357 A1 | 10/1999 |
| WO | WO-01/18051 A2 | 3/2001 |
| WO | WO-01/85790 A2 | 11/2001 |
| WO | WO-03/039485 A2 | 5/2003 |
| WO | WO-2004/042009 A2 | 5/2004 |
| WO | WO-2004/058178 A2 | 7/2004 |
| WO | WO-2004/071517 A2 | 8/2004 |
| WO | WO-2004/081190 A2 | 9/2004 |
| WO | WO-2005/044294 A2 | 5/2005 |
| WO | WO-2005/052157 A1 | 6/2005 |
| WO | WO-2005/079837 A1 | 9/2005 |
| WO | WO-2005/108616 A1 | 11/2005 |
| WO | WO-2006/036922 A2 | 4/2006 |
| WO | WO-2006/068987 A2 | 6/2006 |
| WO | WO-2007/005647 A2 | 1/2007 |
| WO | WO-2007/005955 A2 | 1/2007 |
| WO | WO-2007/024846 A2 | 3/2007 |
| WO | WO-2007/027714 A2 | 3/2007 |
| WO | WO-2007/027761 A2 | 3/2007 |
| WO | WO-2007/076523 A2 | 7/2007 |
| WO | WO-2007/076524 A2 | 7/2007 |
| WO | WO-2007/147019 A2 | 12/2007 |
| WO | WO-2007/149814 A1 | 12/2007 |
| WO | WO-2008/103432 A1 | 8/2008 |
| WO | WO-2008/103473 A1 | 8/2008 |
| WO | WO-2008/106131 A2 | 9/2008 |
| WO | WO-2008/153610 A2 | 12/2008 |
| WO | WO-2009/032954 A1 | 3/2009 |
| WO | WO-2009/043933 A1 | 4/2009 |
| WO | WO-2009/053493 A1 | 4/2009 |
| WO | WO-2009/055936 A1 | 5/2009 |
| WO | WO-2009/073569 A2 | 6/2009 |
| WO | WO-2009/082624 A2 | 7/2009 |
| WO | WO-2010/017598 A1 | 2/2010 |
| WO | WO-2010/027766 A1 | 3/2010 |
| WO | WO-2010/115092 A2 | 10/2010 |
| WO | WO-2010/115786 A1 | 10/2010 |

(56) References Cited

FOREIGN PATENT DOCUMENTS

| | | |
|---|---|---|
| WO | WO-2011/011797 A2 | 1/2011 |
| WO | WO-2011/056600 A1 | 5/2011 |
| WO | WO-2011/066369 A2 | 6/2011 |
| WO | WO-2011/070339 A1 | 6/2011 |
| WO | WO-2011/103105 A1 | 8/2011 |
| WO | WO-2011/104381 A2 | 9/2011 |
| WO | WO-2011/109365 A2 | 9/2011 |
| WO | WO-2011/159655 A2 | 12/2011 |
| WO | WO-2011/159750 A1 | 12/2011 |
| WO | WO-2012/009760 A1 | 1/2012 |
| WO | WO-2012/032181 A2 | 3/2012 |
| WO | WO-2012/061448 A1 | 5/2012 |
| WO | WO-2012/093254 A1 | 7/2012 |
| WO | WO-2012/103345 A1 | 8/2012 |
| WO | WO-2013/165791 A1 | 11/2013 |
| WO | WO-2014/004436 A2 | 1/2014 |
| WO | WO-2014/143540 | 9/2014 |
| WO | WO-2014/149425 A1 | 9/2014 |
| WO | WO-2016/036918 A1 | 3/2016 |
| WO | WO-2017/048901 A1 | 3/2017 |

OTHER PUBLICATIONS

Sofen, H. et al. J. Allergy Clin. Immunol. 133:1032 (Apr. 2014).*
Jabbari, A. et al. Journal of Investigative Dermatology 132:246 (2012; online Aug. 2011).*
Wikipedia entry for "Guselkumab", 5 pages, downloaded May 29, 2018.*
Aggarwal et al., "Interleukin-23 Promotes a Distinct CD4 T Cell Activation State Characterized by the Production of Interleukin-17", Journal of Biological Chemistry, 2003, 278(3): 1910-1914.
Alegre et al., "A Non-Activating "Humanized" Anti-CD3 Monoclonal Antibody Retains Immunosuppressive Properties in Vivo," Transplantation; Jun. 1994, 57(11):1537-1543.
Alunno et al., "Targeting the IL-23/IL-17 axis for the treatment of psoriasis and psoriatic arthritis," Expert Opinion on Biological Therapy, 2015, 15(12):1727-1737.
Anonymous: "A 52-Week, Phase 3, Randomized, Active Comparator and Placebo-Controlled, Parallel Design Study to Evaluate the Efficacy and Safety/Tolerability of Subcutaneous SCH 9000222/MK-3222, Followed by an Optional Long-Term Safety Extension Study, in Subjects with Moderate-to-Severe Chronic Plaque Psoriasis" Dec. 30, 2014, 4 pages, Clinical Trials Identifier: NCT01729754, Clinicaltrials.gov.
Anonymous: "A Phase 2 Multicenter, Randomized, Pacebo- and Active-Comparator-Controlled, Dose-Ranging Trial to Evaluate CNTO 1959 for the Treatment of Subjects with Moderate to Sever Plaque-type Psoriasis (X-PLORE)" Mar. 10, 2014, 4 pages, Clinical Trials Identifier NCT01483599, Clinicaltrials.gov.
Anonymous: "A Phase 2a, Multicenter, Randomized, Double-blind, Placebo-controlled Study Evaluating the Efficacy and Safety of Guselkumab in the Treatment of Subjects with Active Psoriatic Arthritis," Jan. 26, 2015, 4 pages, Clinical Trials Identifier: NCT02319759, Clinicaltrials.gov.
Baerveldt et al., "Ustekinumab improves psoriasis-related gene expression in noninvolved psoriatic skin without inhibition of the antimicrobial response," British Journal of Dermatology, 2013, 168:990-998.
Bandzar et al., "Crohn's disease: A review of treatment options and current research," Cellular Immunology, 2013, 286:45-52.
Beyer et al., "Crystal Structures of the Pro-Inflammatory Cytokine Interleukin-23 and its Complex with a High-Affinity Neutralizing Antibody," Journal of Molecular Biology, 2008, 382:942-955.
Bhambhani et al., "Formulation Design and High-Throughput Excipient Selection Based on Structural Integrity and Conformational Stability of Dilute and Highly Concentrated IgG1 Monoclonal Antibody Solutions," Journal of Pharmaceutical Sciences, 2012, 101(3):1120-1135.

Brodmerkel et al., "The Skin and Circulating Immune Profile of Therapeutic IL-12/23 Blockade in Psoriasis Patients Treated with Ustekinumab," Clinical Immunology, Academic Press, Jan. 1, 2009, 131:S5, Abstract.
Campa et al., "A Review of Biologic Therapies Targeting IL-23 and IL-17 for Use in Moderate-to-Severe Plaque Psoriasis," Dermatology Therapy, 2016, 6:1-12.
Cao et al., "Anti-IL-23 antibody blockade of IL-23/IL-17 pathway attenuates airway obliteration in rat orthotopic tracheal transplantation," International Immunopharmacology, 2011, 11:569-575.
Casset et al., "A peptide mimetic of an anti-CD4 monoclonal antibody by rational design," Biochemical and Biophysical Research Communications, 2003, 307:198-205.
Castro et al., "Reslizumab for Poorly Controlled, Eosinophilic Asthma, A Randomized, Placebo-controlled Study," Am. J. Respir. Crit. Care Med., 2011, 184:1125-1132.
Catalog No. AF1716. "Anti-human IL-23 p19 Antibody," Lot No. JM601., R&D Systems, Inc., Dec. 17, 2003.
Chan et al., "Therapeutic antibodies for autoimmunity and inflammation," Nature Reviews, Immunology, May 2010, 10:301-316.
Choy et al., "Th2 and Th17 inflammatory pathways are reciprocally regulated in asthma," www.ScienceTranslationalMedicine.org, 2015, 7(301):301ra129, 11 pages.
Ciprandi et al., "Serum IL-23 Strongly and Inversely Correlates with FEV1 in Asthmatic Children," International Archives of Allergy and Immunology, 2012, 159(2):183-186.
ClinicalTrials.gov study NCT01018810, published Nov. 24, 2009, (downloaded from https://clinicaltrials.gov/ct2/history/NCT01018810, 6 pages.
ClinicalTrials.gov study NCT01483599, published Nov. 29, 2011 (downloaded from https://clinicaltrials.gov/ct2/history/NCT01483599, 6 pages.
ClinicalTrials.gov study NCT01729754, published Nov. 14, 2012 (downloaded from https://clinicaltrials.gov/ct2/history/NCT01729754, 7 pages.
ClinicalTrials.gov study NCT02031276, published Jan. 8, 2014, 7 pages.
ClinicalTrials.gov study NCT02319759, published Dec. 15, 2014 (downloaded from https://clinicaltrials.gov/ct2/history/NCT02319749), 7 pages.
Croxford et al., IL-12 and IL-23 in health and disease,: Cytokine & Growth Factor Reviews, 2014, 25:415-421.
Cupparic et al., "Serum IL-23 in Asthmatic Children," Journal of Biological Regulators & Homeostatic Agents, 2012, 26(1(S)):53-61.
Daugherty et al., "Formulation and delivery issues for monoclonal antibody therapeutics," Advanced Drug Delivery Reviews, 2006, 58:686-706.
EBioscience, Anti-Mouse IL-23 p 19 Purified; Catalog No. 14-7232; Clone G23-8; According to all information that could be obtained from publicly available sources by Applicants, G23-8 antibody was available for purchase in 2005.
EBioscience, Anti-Mouse IL-23 p 19 Purified; Catalog No. 14-7233; Clone 5B2; According to all information that could be obtained from publicly available sources by Applicants, 5B2 antibody was available for purchase in 2007.
EBioscience, Mouse IL-23 ELISA Ready-Set-Go! ELISA Kit, Catalog No. 88-7923, 6 pages. According to all information that could be obtained from publicly available sources by Applicants, Mouse IL-23 ELISA Ready-Set-Go! ELISA Kit was available for purchase in 2007.
Eijnden, Serge Vanden et al., "Preferential production of the IL-12(p40)/IL-23(19) heterodimer by dendritic cells from human newborns," Eur. J. Immunol., 2006, 36:21-26.
Fahy, John V., "Eosinophilic and Neutrophilic Inflammation in Asthma, Insights from Clinical Studies," Proceedings of the American Thoracic Society, 2009, 6:256-259.
Ferrara et al., "Recombinant renewable polyclonal antibodies," mABs, 2015, 7(1):32-41.
Fichtner-Feigl et al., "Treatment of murine Th1- and Th2-mediated inflammatory bowel disease with NF-kB decoy oligonucleotides," Journal of Clinical Investigation, Nov. 2005, 115(11):3057-3071.

(56) References Cited

OTHER PUBLICATIONS

Gaffen et al., "The IL-23-1L-17 immune axis: from mechanisms to therapeutic testing," Nature Reviews, 2014, 14:585-600.
Gordon et al., "A Phase 2 Trial of Guselkumab versus Adalimumab for Plaque Psoriasis," New England Journal of Medicine, 2015, 373(2):136-144.
Gudjonsson et al., "Assessment of the Psoriatic Transcriptome in a Large Sample: Additional Regulated Genes and Comparisons with in Vitro Models," Journal of Investigative Dermatology, 2010, 130:1829-1840.
Haldar et al., "Mepolizumab and Exacerbations of Refractory Eosinophilic Asthma," The New England Journal of Medicine, 2009, 360:973-984.
Happel et al., "Divergent roles of IL-23 and IL-12 in host defense against Klebsiella pneumoniae" Journal of Experimental Medicine, Sep. 2005, 202(6):761-769.
Hegazi et al., "Carbon monoxide ameliorates chronic murine colitis through a heme oxygenase 1-dependent pathway," Journal of Experimental Medicine, Dec. 2005, vol. 202, No. 12, pp. 1703-1713.
Hegyi et al., "Vitamin D Analog Calcipotriol Suppresses the Th17 Cytokine-Induced Proinflammatory S100 'Alarmins' Psoriasin (S100A7) and Koebnerisin (S100A15) in Psoriasis," Journal of Investigative Dermatology, 2012, 132:1416-1424.
Hoeve et al., "IL-12 receptor deficiency revisited: IL-23-mediated signaling is also impaired in human genetic IL-12 receptor ?1deficiency," Eur. J. Immunol., 2003, 33:3393-3397.
Hu et al., "Information contributed by meta-analysis in exposure-response modeling: application to phase 2 dose selection of guselkumab in patients with moderate-to-severe psoriasis," Journal of Pharmacokinet. Pharmacodyn., 2014, 41:239-250.
International Preliminary Report on Patentability and Written Opinion for PCT/US2015/041706 dated Feb. 2, 2017.
International Preliminary Report on Patentability for PCT/US2011/058869 dated May 7, 2013.
International Search Report & Written Opinion for PCT/US2011/058869, dated Feb. 27, 2012.
International Search Report and Written Opinion dated Jul. 28, 2017, in PCT/US2017/027332.
International Search Report and Written Opinion dated Oct. 26, 2017 in PCT/US2016/027263.
International Search Report for PCT/US2013/038109 dated Apr. 25, 2013.
International Search Report for PCT/US2015/041706 dated Oct. 15, 2015.
International Search Report for PCT/US2016/016061 dated May 18, 2016.
International Search Report for PCT/US2016/027263 dated Jun. 29, 2016.
International Search Report for PCT/US2016/051844 dated Jan. 10, 2017.
Irvin et al., "Increased frequency of dual-positive TH2/TH17 cells in bronchoalveolar lavage fluid characterizes a population of patients with severe asthma," Journal of Allergy and Clinical Immunology, 2014, 134(5):1175-1186.
Kastelein et al., "Discovery and Biology of IL-23 and IL-27: Related but Functionally Distinct Regulators of Inflammation," Annual Reviews Immunology, 2007, 25: 221-242.
Kerdel et al., "An evolution in switching therapy for psoriasis patients who fail to meet treatment goals," Dermatologic Therapy, 2015, 28:390-403.
Kidoya et al., "Fas Ligand Induces Cell-Autonomous IL-23 Production in Dendritic Cells, a Mechanism for Fas Ligand-Induced IL-17 Production," Journal of Immunology, 2005, 8024-8031.
Kikly et al., "The IL-23/Th17 axis: Therapeutic targets for autoimmune inflammation," Current Opinion in Immunology, 2006, 18:670-675.
Kim et al., "Diagnosis and management of psoriasis," Canadian Family Physician, 2017, 63:278-285.
Kofoed et al "New Drugs and Treatment Targets in Psoriasis," Acta Derm. Venereol., 2015, 95:133-139.
Kopp et al., "Clinical improvement in psoriasis with specific targeting of interleukin-23," Nature, 2015, 521(7551):222-226.
Krishnan et al., "Development of Formulations for Therapeutic Monoclonal Antibodies and Fc Fusion Proteins," Formulation and Process Development Strategies for Manufacturing Biopharmaceuticals, 2010, Chapter 16, 383-427.
Krueger et al., "Anti-IL-23A mAb BI 655066 for treatment of moderate-to-severe psoriasis: Safety, efficacy, pharmacokinetics, and biomarker results of a single-rising-dose, randomized, double-blind, placebo-controlled trial," Journal of Allergy and Clinical Immunology, 136:116-124, 2015.
Kuwashima et al., "Delivery of Dendritic Cells Engineered to Secrete IFN-? into Central Nervous System Tumors Enhances the Efficacy of Peripheral Tumor Cell Vaccines: Dependence on Apoptotic Pathways," Journal of Immunology, 2005, 175: 2730-2740.
Langowski et al,. "IL-23 promotes tumour incidence and growth," Nature, Jul. 2006, 442(27):461-465.
Lee et al., "Increased Expression of Interleukin 23 p19 and p40 in Lesional Skin of Patients with Psoriasis Vulgaris," Journal of Experimental Medicine, 2004, 199(1):125-130.
Leonardi et al., "Efficacy and safety of ustekinumab, a human interleukin-12/23 monoclonal antibody, in patients with psoriasis: 76-weeks results form a randomised, double-blind, placebo-controlled trail (PHOENIX 1)," The Lancet, 2008, 371:1665-1674.
Li et al., "Silencing IL-23 expression by a small hairpin RNA protects against asthma in mice," Experimental and Molecular Medicine, 2011, 43(4):197-204.
MacCallum et al., "Antibody-antigen Interactions: Contact Analysis and Binding Site Topography," J. Mol. Biol., 1996, 262:732-745.
Mallbris et al., "Neutrophil gelatinase-associated lipocalin is a marker for dysregulated keratinocyte differentiation in human skin" Experimental Dermatology, 2002, 11:584-591.
McInnes et al., "Efficacy and safety of secukinumab, a fully human anti-interleukin-17A monoclonal antibody, in patients with moderate-to-severe psoriatic arthritis: a 24-week, randomised, double-blind, placebo-controlled, phase II proof-of-concept trail," Ann. Rheum. Dis., 2014, 73:349-356.
McKinley et al., "TH17 Cells Mediate Steroid-Resistant Airway Inflammation and Airway Hyperresponsiveness in Mice," The Journal of Immunology, 2008, 181:4089-4097.
Morelli et al., "CD4+ T Cell Responses Elicted by Different Subsets of Human Skin Migratory Dendritic Cells," The Journal of Immunology, 2005, 175:7905-7915.
Naji et al., "T Helper 17 Cells and Related Cytokines after Allergen Inhalation Challenge in Allergic Asthmatics," International Archives of Allergy & Immunology, 2014, 165:27-34.
Nakajima et al., "Role of IL-23 and Th17 Cells in Airway Inflammation in Asthma," Immune Network, 2010, 10(1):1-4.
Narasimhan et al., "High-dose monoclonal antibodies via the subcutaneous route: challenges and technical solutions, an industry perspective," Therapeutic Delivery, 2012, 3(7):889-900.
Oppmann et al., Novel p19 Protein Engages IL-12p40 to Form a Cytokine, IL-23, with Biological Activities Similar as Well as Distinct from IL-12,$201D Immunity, 2000, 13:715-725.
Papp et al., "Tildrakizumab (MK-3222) an anti-interleukin-23p19 monoclonal antibody, improves psoriasis in a phase IIb randomized placebo-controlled trial," British Journal of Dermatology, 2015, 173:930-939.
Parham et al., "A Receptor for the Heterodimeric Cytokine IL-23 is Composed of IL-12Rß1 and a Novel Cytokine Receptor Subunit, IL-23R," Journal of Immunology, 2002, 168:5699-5708.
Patel et al., "Emerging Therapies for the Treatment of Psoriasis,," Dermatol Ther. (Heidelb), 2012, 2:16, 10 pages.
Paul, William E., M.D., Fundamental Immunology, 3rd Ed., Raven Press, New York, Chapter 8, 1993, 292-295.
Pirhonen et al., "Regulation of Virus-Induced IL-12 and IL-23 Expression in Human Macrophages," Journal of Immunology, 2002, 5673-5678.
Piskin et al., "Clinical Improvement in chronic plaque-type psoriasis lesions after narrow-band UVB therapy is accompanied by a decrease in the expression of IFN-y inducers—IL-12, IL-18, and IL-23," Experimental Dermatology, 2004, 13:764-772.

(56) References Cited

OTHER PUBLICATIONS

Piskin, Gamze "IL-23 Expression by Keratinocytes," Effects of Therapies on Cytokine Patterns of Psoriasis, 2004, Chapter 7, 114-131.

R&D Systems New Products, Jun. 2005. 12 pgs. www.RnDSystems.com.

R&D Systems, de novo newsletter, Mar. 2004, 10 pgs. www.rndsystems.com.

Rouet et al., "Stability engineering of the human antibody repertoire," FEBS Letters, 2014, 588:269-277.

Sands et al., "A randomized, double-blind placebo-controlled phase 2a induction study of MEDI2070 (anti-p19 antibody) in patients with active Crohn's disease who have failed anti-TNF antibody therapy," Journal of Crohn's and Colitis, Feb. 1, 2015, 9(Supp_1):S15-S16, OP025.

Savage et al. "Ustekinumab in the Treatment of Psoriasis and Psoriatic Arthritis," Rheumatol. Ther., 2015, 2:1-16.

Sehy et al., Abstract 560.34 "Unambiguous Detection of IL-23 (p19/p40) Protein in Native Samples Using a Novel Enzyme-Linked Immunosorbent Assay," Experimental Biology, 2005, A945-A946, International Congress of Physiological Sciences.

Shire, Steven J., Monoclonal Antibodies: Meeting the Challenges in Manufacturing, Formulation, Delivery and Stability of Final Drug Product, 2015.

Singh et al., "Selective targeting of the IL23 pathway: Generation and characterization of a novel high-affinity humanized anti-IL23A antibody," MABS, Apr. 23, 2015, 7(4):778-791.

Sofen et al., "Guselkumab (an IL-23-specific mAb) demonstrates clinical and molecular response in patients iwth moderate-to-severe psoriasis," Journal of Allergy and Clinical Immunology, 2014,133:1032-1040.

Suarez-Farinas et al., "Expanding the Psoriasis Disease Profile: Interrogation of the Skin and Serum of Patients with Moderate-to-Severe Psoriasis," Journal of Investigative Dermatology, 2012, 132:2552-2564.

Tang et al., "Interleukin-23: as a drug target for autoimmune inflammatory diseases," Immunology, 2011, 135:112-124.

Tian et al., "Meta-Analysis Derived (MAD) Transcriptome of Psoriasis Defines the "Core" Patheogenesis of Disease," PLOS One, 2012, 7(9):e44274, 15 pages.

U.S. Appl. No. 13/870,061, filed Apr. 25, 2013. First named inventor: Gerald Henry Nabozny.

U.S. Appl. No. 14/302,986, filed Jun. 12, 2014. First named inventor: Rachel Rebecca Barrett.

Vajdos et al., "Comprehensive Functional Maps of the Antigen-binding Site of an Anti-ErbB2 Antibody Obtained with Shotgun Scanning Mutagenesis," J. Mol. Biol., 2002, 320:415-428.

Verreck et al., "Human IL-23—producing type 1 macrophages promote but IL-10 producing type 2 macrophages subvert immunity to (myco)bacteria," PNAS, 2004, 101(13):4560-4565.

Wakashin et al., "IL-23 and Th17 Cells Enhance Th2-Cell-mediated Eosinophilic Airway Inflammation in Mice" American Journal of Respiratory and Critical Care Medicine, 2008, 178:1023-1032.

Wang et al,. "Antibody Structure, Instability, and Formulation," Journal of Pharmaceutical Sciences, Jan. 1, 2007, 96(1):1-26.

Wang et al., Aggregation of Therapeutic Proteins, 2010.

Wang, Wei, "Review: Instability, stabilization, and formulation of liquid protein pharmaceuticals," International Journal of Pharmaceutics, 1999, 185:129-188.

Wenzel, Sally, "Severe asthma: from characteristics to phenotypes to endotypes," Clinical & Experimental Allergy, 2012, 42:650-658.

Woodle et al., "Phase I Trial of a Humanized, Fc Receptor Non-binding OKT3 Antibody, huOKT3γ1(Ala-Ala) In the Treatment of Acute Renal Allograft Rejection," Transplantation, 1999, 68(5):608-616.

Written Opinion dated Aug. 17, 2017, in PCT/US2016/016061.

Yannam et al., "IL-23 in Infections, Inflammation, Autoimmunity and Cancer: Possible Role in HIV-1 and AIDS," Journal of Neuroimmune Pharmacology, 2012, 7:95-112.

Yeilding et al., "Development of the IL-12/23 antagonist ustekinumab in psoriasis: past, present and future perspectives," Annals of the New York Academy of Sciences, 2011, 1222:30-39.

Zakharova et al., "Paradoxical Anti-Inflammatory Actions of TNF -a: Inhibition of IL-12 and IL-23 via TNF Receptor 1 in Macrophages and Dendritic Cells" Journal of Immunology, 2005, 175:5024-5033.

BioPorto Product Catalog, 2010, 28 pps.

Chiricozzi, A. et al., Role of IL-23 in the pathogenesis of psoriasis: a novel potential therapeutic target?, Expert Opinion Ther. Targets, vol. 18, pp. 1-13, 2014.

CircuLex Main Products Catalog, 3 pps., 2010.

Usui, T., The relationship between oral mucosal immunity and activity of dental caries strenuous exercise, Descente Sports Science, vol. 35, pp. 37-43, 2014.

International Preliminary Report on Patentability and Written Opinion for PCT/US2017/027332 dated Oct. 16, 2018.

Boehringer Ingelheim, Bl 655066 Dose Ranging in Psoriasis, Active Comparator Ustekinumab. Available from: https://clinicaltrials.gov/ct2/show/NCT02054481. NLM identifier. NCT 02054481. First posted Feb. 4, 2014.

Karon, A, I L-23 inhibitor topped ustenkinumab against psoriasis. M Dedge ™Rheumatology. Retrieved from www.mdedge.com/rheumatology, 3 pps. dated Apr. 2, 2015.

\* cited by examiner

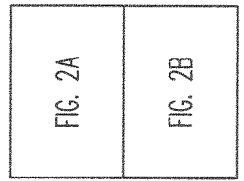

SEQUENCE LISTING

```
<160> NUMBER OF SEQ ID NOS: 23

<210> SEQ ID NO 1
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Lys Ala Ser Arg Asp Val Ala Ile Ala Val Ala
1               5                   10

<210> SEQ ID NO 2
<211> LENGTH: 7
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Trp Ala Ser Thr Arg His Thr
1               5

<210> SEQ ID NO 3
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

His Gln Tyr Ser Ser Tyr Pro Phe Thr
1               5

<210> SEQ ID NO 4
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Asn Thr Phe Thr Asp Gln Thr Ile His
1               5                   10

<210> SEQ ID NO 5
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Tyr Ile Tyr Pro Arg Asp Asp Ser Pro Lys Tyr Asn Glu Asn Phe Lys
1               5                   10                  15

Gly

<210> SEQ ID NO 6
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Pro Asp Arg Ser Gly Tyr Ala Trp Phe Ile Tyr
1               5                   10

<210> SEQ ID NO 7
<211> LENGTH: 10
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 7

Gly Tyr Thr Phe Thr Asp Gln Thr Ile His
1               5                   10

<210> SEQ ID NO 8
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Gly Phe Thr Phe Thr Asp Gln Thr Ile His
1               5                   10

<210> SEQ ID NO 9
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Gly Gly Thr Phe Thr Asp Gln Thr Ile His
1               5                   10

<210> SEQ ID NO 10
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Leu
        35                  40                  45

Phe Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Leu Ala Asp Tyr Tyr Cys His Gln Tyr Ser Ser Tyr Pro Phe
                85                  90                  95

Thr Phe Gly Gln Gly Thr Lys Leu Glu Ile Lys
            100                 105

<210> SEQ ID NO 11
<211> LENGTH: 107
<212> TYPE: PRT
<213> ORGANISM: Artificial Sequence
<220> FEATURE:
<221> NAME/KEY: source
```

-continued

<223> OTHER INFORMATION: /note="Description of Artificial Sequence:
      Synthetic polypeptide"

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys
            100                 105

<210> SEQ ID NO 12
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Leu
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Thr Tyr Tyr Cys His Gln Tyr Ser Ser Tyr Pro Phe
                85                  90                  95

Thr Phe Gly Ser Gly Thr Lys Leu Glu Ile Lys
            100                 105

<210> SEQ ID NO 13
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Leu
        35                  40                  45

Phe Trp Ala Ser Thr Arg His Thr Gly Val Pro Asp Arg Phe Ser Gly
            50                  55                  60

Ser Gly Ser Arg Thr Asp Phe Thr Leu Thr Ile Ser Ser Leu Gln Pro
65                  70                  75                  80

Glu Asp Leu Ala Asp Tyr Tyr Cys His Gln Tyr Ser Tyr Pro Phe
                85                  90                  95

Thr Phe Gly Ser Gly Thr Lys Leu Glu Ile Lys
            100                 105

<210> SEQ ID NO 14
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Gln
                20                  25                  30

Thr Ile His Trp Met Arg Gln Ala Pro Gly Gln Gly Leu Glu Trp Ile
            35                  40                  45

Gly Tyr Ile Tyr Pro Arg Asp Asp Ser Pro Lys Tyr Asn Glu Asn Phe
        50                  55                  60

Lys Gly Lys Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Pro Asp Arg Ser Gly Tyr Ala Trp Phe Ile Tyr Trp Gly Gln
                100                 105                 110

Gly Thr Leu Val Thr Val Ser Ser
            115                 120

<210> SEQ ID NO 15
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Gln
                20                  25                  30

Thr Ile His Trp Val Arg Gln Ala Pro Gly Gln Gly Leu Glu Trp Met
            35                  40                  45

Gly Tyr Ile Tyr Pro Arg Asp Asp Ser Pro Lys Tyr Asn Glu Asn Phe
        50                  55                  60

Lys Gly Lys Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Pro Asp Arg Ser Gly Tyr Ala Trp Phe Ile Tyr Trp Gly Gln
                100                 105                 110

Gly Thr Leu Val Thr Val Ser Ser
        115                 120

<210> SEQ ID NO 16
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Gln Val Gln Leu Val Gln Ser Gly Ala Glu Val Lys Lys Pro Gly Ser
1               5                   10                  15

Ser Val Lys Thr Ser Cys Lys Ala Ser Gly Gly Thr Phe Thr Asp Gln
                20                  25                  30

Thr Ile His Trp Val Arg Gln Arg Pro Gly Gln Gly Leu Glu Trp Met
            35                  40                  45

Gly Tyr Ile Tyr Pro Arg Asp Asp Ser Pro Lys Tyr Asn Glu Asn Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Pro Asp Arg Ser Gly Tyr Ala Trp Phe Ile Tyr Trp Gly Gln
                100                 105                 110

Gly Thr Leu Val Thr Val Ser Ser
        115                 120

<210> SEQ ID NO 17
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Thr Asp Gln
                20                  25                  30

Thr Ile His Trp Val Arg Gln Ala Pro Gly Gln Gly Leu Glu Trp Met
            35                  40                  45

Gly Tyr Ile Tyr Pro Arg Asp Asp Ser Pro Lys Tyr Asn Glu Asn Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Pro Asp Arg Ser Gly Tyr Ala Trp Phe Ile Tyr Trp Gly Gln
                100                 105                 110

Gly Thr Leu Val Thr Val Ser Ser
        115                 120

```
<210> SEQ ID NO 18
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 19
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Gln
            20                  25                  30

Thr Ile His Trp Met Arg Gln Ala Pro Gly Gln Gly Leu Glu Trp Ile
        35                  40                  45

Gly Tyr Ile Tyr Pro Arg Asp Asp Ser Pro Tyr Asn Glu Asn Phe
    50                  55                  60

Lys Gly Lys Val Thr Ile Thr Ala Asp Lys Ser Thr Ser Thr Ala Tyr
65                  70                  75                  80
```

Met Glu Leu Ser Ser Leu Arg Ser Glu Asp Thr Ala Val Tyr Tyr Cys
                85                  90                  95

Ala Ile Pro Asp Arg Ser Gly Tyr Ala Trp Phe Ile Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 20
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 20

| | | | | | | | | | | | |
|---|---|---|---|---|---|---|---|---|---|---|---|
| Gln | Val | Gln | Leu | Val | Gln | Ser | Gly | Ala | Glu | Val | Lys | Lys | Pro | Gly | Ser |
| 1 | | | | 5 | | | | | 10 | | | | | 15 | |
| Ser | Val | Lys | Val | Ser | Cys | Lys | Ala | Ser | Gly | Phe | Thr | Phe | Thr | Asp | Gln |
| | | | 20 | | | | | 25 | | | | | 30 | | |
| Thr | Ile | His | Trp | Val | Arg | Gln | Ala | Pro | Gly | Gln | Gly | Leu | Glu | Trp | Met |
| | | 35 | | | | | 40 | | | | | 45 | | | |
| Gly | Tyr | Ile | Tyr | Pro | Arg | Asp | Asp | Ser | Pro | Lys | Tyr | Asn | Glu | Asn | Phe |
| | 50 | | | | | 55 | | | | | 60 | | | | |
| Lys | Gly | Lys | Val | Thr | Leu | Thr | Ala | Asp | Lys | Ser | Thr | Ser | Thr | Ala | Tyr |
| 65 | | | | | 70 | | | | | 75 | | | | | 80 |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Ala | Ile | Pro | Asp | Arg | Ser | Gly | Tyr | Ala | Trp | Phe | Ile | Tyr | Trp | Gly | Gln |
| | | | 100 | | | | | 105 | | | | | 110 | | |
| Gly | Thr | Leu | Val | Thr | Val | Ser | Ser | Ala | Ser | Thr | Lys | Gly | Pro | Ser | Val |
| | | | 115 | | | | | 120 | | | | | 125 | | |
| Phe | Pro | Leu | Ala | Pro | Ser | Ser | Lys | Ser | Thr | Ser | Gly | Gly | Thr | Ala | Ala |
| | 130 | | | | | 135 | | | | | 140 | | | | |
| Leu | Gly | Cys | Leu | Val | Lys | Asp | Tyr | Phe | Pro | Glu | Pro | Val | Thr | Val | Ser |
| 145 | | | | | 150 | | | | | 155 | | | | | 160 |
| Trp | Asn | Ser | Gly | Ala | Leu | Thr | Ser | Gly | Val | His | Thr | Phe | Pro | Ala | Val |
| | | | | 165 | | | | | 170 | | | | | 175 | |
| Leu | Gln | Ser | Ser | Gly | Leu | Tyr | Ser | Leu | Ser | Ser | Val | Val | Thr | Val | Pro |
| | | | 180 | | | | | 185 | | | | | 190 | | |
| Ser | Ser | Ser | Leu | Gly | Thr | Gln | Thr | Tyr | Ile | Cys | Asn | Val | Asn | His | Lys |
| | | | 195 | | | | | 200 | | | | | 205 | | |
| Pro | Ser | Asn | Thr | Lys | Val | Asp | Lys | Arg | Val | Glu | Pro | Lys | Ser | Cys | Asp |
| | 210 | | | | | 215 | | | | | 220 | | | | |
| Lys | Thr | His | Thr | Cys | Pro | Pro | Cys | Pro | Ala | Pro | Glu | Ala | Ala | Gly | Gly |
| 225 | | | | | 230 | | | | | 235 | | | | | 240 |
| Pro | Ser | Val | Phe | Leu | Phe | Pro | Pro | Lys | Pro | Lys | Asp | Thr | Leu | Met | Ile |
| | | | | 245 | | | | | 250 | | | | | 255 | |
| Ser | Arg | Thr | Pro | Glu | Val | Thr | Cys | Val | Val | Val | Asp | Val | Ser | His | Glu |
| | | | 260 | | | | | 265 | | | | | 270 | | |
| Asp | Pro | Glu | Val | Lys | Phe | Asn | Trp | Tyr | Val | Asp | Gly | Val | Glu | Val | His |
| | | | 275 | | | | | 280 | | | | | 285 | | |
| Asn | Ala | Lys | Thr | Lys | Pro | Arg | Glu | Glu | Gln | Tyr | Asn | Ser | Thr | Tyr | Arg |
| | 290 | | | | | 295 | | | | | 300 | | | | |
| Val | Val | Ser | Val | Leu | Thr | Val | Leu | His | Gln | Asp | Trp | Leu | Asn | Gly | Lys |
| 305 | | | | | 310 | | | | | 315 | | | | | 320 |
| Glu | Tyr | Lys | Cys | Lys | Val | Ser | Asn | Lys | Ala | Leu | Pro | Ala | Pro | Ile | Glu |
| | | | | 325 | | | | | 330 | | | | | 335 | |
| Lys | Thr | Ile | Ser | Lys | Ala | Lys | Gly | Gln | Pro | Arg | Glu | Pro | Gln | Val | Tyr |
| | | | 340 | | | | | 345 | | | | | 350 | | |
| Thr | Leu | Pro | Pro | Ser | Arg | Glu | Glu | Met | Thr | Lys | Asn | Gln | Val | Ser | Leu |
| | | | 355 | | | | | 360 | | | | | 365 | | |
| Thr | Cys | Leu | Val | Lys | Gly | Phe | Tyr | Pro | Ser | Asp | Ile | Ala | Val | Glu | Trp |
| | 370 | | | | | 375 | | | | | 380 | | | | |
| Glu | Ser | Asn | Gly | Gln | Pro | Glu | Asn | Asn | Tyr | Lys | Thr | Thr | Pro | Pro | Val |
| 385 | | | | | 390 | | | | | 395 | | | | | 400 |

-continued

```
Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 21
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Leu
        35                  40                  45

Phe Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Leu Ala Asp Tyr Tyr Cys His Gln Tyr Ser Ser Tyr Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 22
<211> LENGTH: 189
<212> TYPE: PRT
<213> ORGANISM: Homo sapiens

<400> SEQUENCE: 22

Met Leu Gly Ser Arg Ala Val Met Leu Leu Leu Leu Pro Trp Thr
1               5                   10                  15

Ala Gln Gly Arg Ala Val Pro Gly Gly Ser Ser Pro Ala Trp Thr Gln
            20                  25                  30
```

```
Cys Gln Gln Leu Ser Gln Lys Leu Cys Thr Leu Ala Trp Ser Ala His
            35                  40                  45

Pro Leu Val Gly His Met Asp Leu Arg Glu Glu Gly Asp Glu Glu Thr
    50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
                85                  90                  95

Leu Ile Phe Tyr Glu Lys Leu Leu Gly Ser Asp Ile Phe Thr Gly Glu
            100                 105                 110

Pro Ser Leu Leu Pro Asp Ser Pro Val Gly Gln Leu His Ala Ser Leu
            115                 120                 125

Leu Gly Leu Ser Gln Leu Leu Gln Pro Glu Gly His His Trp Glu Thr
    130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185

<210> SEQ ID NO 23
<211> LENGTH: 4
<212> TYPE: PRT
<213> ORGANISM: Unknown
<220> FEATURE:
<221> NAME/KEY: source
<223> OTHER INFORMATION: /note="Description of Unknown: 'DEAD' box motif
      peptide"

<400> SEQUENCE: 23

Asp Glu Ala Asp
1
```

BIOMARKERS USEFUL IN THE TREATMENT OF IL-23A RELATED DISEASES

SEQUENCE LISTING

The instant application contains a Sequence Listing which has been submitted electronically in ASCII format and is hereby incorporated by reference in its entirety. Said ASCII copy, created on Jul. 16, 2015, is named 09-0632-WO-1_SL.txt and is 25,626 bytes in size.

TECHNICAL FIELD OF THE INVENTION

This invention generally relates to biomarkers useful in the treatment of IL-23A related diseases, in particular inflammatory diseases such as psoriasis. The invention also relates to methods of using the biomarkers disclosed herein, for example in therapies utilizing IL-23A antagonists.

BACKGROUND OF THE INVENTION

Psoriasis is a chronic, immune-mediated, inflammatory skin disease, with a global incidence of approximately 2%, associated with significant morbidity and can have a substantial psychosocial impact on quality of life and well-being of patients. Plaque psoriasis is the most common form and affects approximately 80-90% of patients, manifesting as raised plaques on the skin; the disease usually begins in late adolescence and early adulthood and may persist through adult life. The extent of the affected body surface area (BSA) and the degree of skin manifestations, including erythema, induration, and scaling, defines the severity of psoriasis with approximately 20-30% of patients having moderate-to-severe disease.

Psoriasis is a multifactorial disease, of unknown aetiology, with autoimmune and autoinflammatory components. Multiple genome-wide association studies have linked variants in the genes for the IL-23 receptor to psoriasis susceptibility. Human IL-23 is primarily produced by antigen presenting cells and induces differentiation of T helper 17 (Th17) cells. This results in the production of IL-17 and IL-22, which may mediate the development of the epidermal hyperplasia and tissue inflammation observed in psoriasis.

There is therefore a need for improved means to follow the efficacy of treatment options against psoriasis, identify patients that will most benefit from these treatments in Psoriasis and other inflammatory diseases, and to determine and adjust the dosages of therapies for patients as may be needed.

SUMMARY OF THE INVENTION

The present invention addresses the above needs and provides biomarkers useful in the treatment of IL-23A related diseases.

In one embodiment, the present invention provides a method for detecting the presence or absence of a beneficial response in a patient after administration of an IL-23A antagonist, comprising: a) obtaining a biological sample from the patient; b) measuring in said sample the level of expression of one or more biomarkers; c) comparing the level to control value of the level of the biomarkers; and d) determining whether or not the difference in levels between the sample and the control reflects a beneficial response in the patient, wherein the one or more biomarkers are genes/proteins associated with the IL-23/IL-17 axis (for example one or more of IL-23A, IL-23R, IL-22, IL-22RA1 RA2, IL-17A, IL-17F, IL-17RA, and IL-17RC), keratinocyte and epithelial cell differentiation (for example one or more of late cornified envelope protein, transglutaminase 1, and cornifelin), tissue inflammation (for example one or more of β-defensin 2, neutrophil gelatinase lipocalin, and S-100 proteins) or the IFNα pathway (for example one or more of IFIH1, ISG15, IRF7, IFI44, MX1, MX2, STAT1, and TRIM22).

In one embodiment, the presence or absence of a beneficial response in the patient is detected prior to and after administration of the IL-23A antagonist.

In one embodiment, the control value of the value of a patient treated with a placebo. In one embodiment, the control value of the value of a patient treated with a placebo and the difference is the difference between the sample from a patient treated with the IL-23A antagonist and the placebo.

In one embodiment, the level of the gene or the protein of said one or more biomarker is measured. In one embodiment, the patient suffers from psoriasis.

In one embodiment, the control value is calculated using samples from subjects that do not suffer from psoriasis. In one embodiment, the control value, for example the placebo value, is determined using samples from known psoriasis patients, for example from placebo-treated psoriasis patients. In one embodiment, the control value is determined using at least one previous sample taken from the patient.

In one embodiment, the one or more biomarkers is S-100A7, neutrophil gelatinase lipocalin or β-defensin 2. In one embodiment, the biological sample is a skin biopsy, blood, plasma or serum sample. In one embodiment, the IL-23A antagonist is an anti-IL-23A antibody or an antigen binding fragment thereof. In one embodiment, the levels of biomarkers are determined by RNA sequencing or ELISA or another protein assay.

In one embodiment, the method further comprises continuing the administration of the IL-23A antagonist to the patient if the difference in levels between the sample and the control reflects a beneficial response in the patient. In one embodiment, the method further comprises continuing the administration of the IL-23A antagonist to the patient if the difference in levels from a patient treated with the antagonist versus the placebo reflects a beneficial response in the patient.

In a further embodiment, the present invention provides a method of determining whether a potential therapeutic agent is efficacious in the treatment of psoriasis comprising: a) obtaining a first biological sample from a psoriasis patient prior to being treated with the potential therapeutic agent; b) treating the psoriasis patient with the potential therapeutic agent; c) obtaining a second biological sample from the psoriasis patient after being treated with the potential therapeutic agent; d) measuring in said first and second sample the levels of expression of one or more biomarkers; and e) comparing the biomarker levels in the second sample to the levels in the first sample, wherein lower biomarker levels in the second sample than in the first sample indicate that the potential therapeutic agent is efficacious, and further wherein the one or more biomarkers are genes associated with the IL-23/IL-17 axis (for example one or more of IL-23A, IL-23R, IL-22, IL-22RA1 RA2, IL-17A, IL-17F, IL-17RA, and IL-17RC), keratinocyte and epithelial cell differentiation (for example one or more of late cornified envelope protein, transglutaminase 1, and cornifelin), tissue inflammation (for example one or more of β-defensin 2, neutrophil gelatinase lipocalin, and S-100 proteins) and the IFNα pathway (for example one or more of IFIH1, ISG15, IRF7, IFI44, MX1, MX2, STAT1, and TRIM22). In one embodiment, said step e) comprises comparing the biomarker levels in the second sample to the levels in the first sample, wherein lower biomarker levels in the second sample than in the first sample and correlation with improvement in a clinical efficacy measure ie PASI scores in case of Psoriasis indicates the potential therapeutic agent is efficacious.

In one embodiment, the method further comprises continuing the treatment of the patient if biomarker levels in the second sample is lower than the levels in the first sample.

In a further embodiment, the present invention provides a method of treating psoriasis in a subject comprising: a) determining whether to initiate treatment of the subject, modify the treatment dose, modify the dosing interval, or discontinue treatment, based on the method of any of the preceding claims; and b) modifying the treatment regimen based on the determination.

In a further embodiment, the present invention provides a method of monitoring patient response to a psoriasis treatment comprising:
  a) obtaining a first biological sample from the patient;
  b) measuring the level of one or more biomarkers in said first biological sample, wherein said one or more biomarkers are genes/proteins associated with the IL-23/IL-17 axis (for example one or more of IL-23A, IL-23R, IL-22, IL-22RA1 RA2, IL-17A, IL-17F, IL-17RA, and IL-17RC), keratinocyte and epithelial cell differentiation (for example one or more of late cornified envelope protein, transglutaminase 1, and cornifelin), tissue inflammation (for example one or more of β-defensin 2, neutrophil gelatinase lipocalin, and S-100 proteins) and the IFNα pathway (for example one or more of IFIH1, ISG15, IRF7, IFI44, MX1, MX2, STAT1, and TRIM22);
  c) administering a treatment compound to the patient;
  d) obtaining a second biological sample from the patient;
  e) measuring the level of said one or more biomarkers in said second biological sample; and
  f) comparing the levels of the one or more biomarkers obtained from first and second biological samples;
  wherein a decreased level of the one or more biomarkers in the second biological sample indicates an effective response. In one aspect, a decreased level of the one or more biomarkers in the second biological sample and correlation with improvement in a clinical efficacy measure ie PASI scores in case of Psoriasis indicates an effective response.

In a further embodiment, the present invention provides a method for monitoring patient compliance with a drug treatment protocol for psoriasis comprising:
  a) obtaining a biological sample from said patient;
  b) measuring the level of one or more biomarkers, wherein the one or more biomarkers are genes/proteins associated with the IL-23/IL-17 axis (for example one or more of IL-23A, IL-23R, IL-22, IL-22RA1 RA2, IL-17A, IL-17F, IL-17RA, and IL-17RC), keratinocyte and epithelial cell differentiation (for example one of more of late cornified envelope protein, transglutaminase 1, and cornifelin), tissue inflammation (for example one of more of β-defensin 2, neutrophil gelatinase lipocalin, and S-100 proteins) and the IFNα pathway (for example one of more of IFIH1, ISG15, IRF7, IFI44, MX1, MX2, STAT1, and TRIM22); and
  c) determining if the level is decreased in the patient sample compared to the level in a control untreated sample;
  wherein a decreased level indicates patient compliance with said drug treatment protocol.

In one embodiment, in any one of the methods above, the level of the one or more biomarkers in the second biological sample is decreased by at least about 20%, 25%, 30%, 35%, 40%, 45%, 50%, 55%, 60%, 65%, 65%, 70%, 75%, 80%, 85%, 90%, or 95% or more as compared to the level in the first biological sample.

In one embodiment, in any one of the methods above, the biological sample is a skin biopsy, blood, plasma or serum sample. In one embodiment, in any one of the methods above, the IL-23A antagonist is an anti-IL-23A antibody or an antigen binding fragment thereof. In one embodiment, in any one of the methods above, the levels of biomarkers are determined by RNA sequencing or ELISA or another protein assay.

In one embodiment, the present invention further provides a method of selecting a patient, for example using a method disclosed herein. In one embodiment, the present invention further provides a method of enriching a patient population for patients expected to have a beneficial response after treatment with an IL-23 antagonist, for example using a method of the present invention. In one embodiment, the present invention further provides a method of enriching a patient population for patients expected to have a beneficial response prior to or early after treatment with an IL-23 antagonist, for example using a method of the present invention.

In a further embodiment, the present invention further provides an ELISA kit comprising one or more antibodies or antigen binding fragments thereof that specifically bind to one or more biomarkers, wherein the one or more biomarkers is ieS-100 proteins, neutrophil gelatinase lipocalin or β-defensin 2. In one embodiment, the ELISA or other protein assay kit further comprises instructions for use of the kit prior to treatment or for monitoring psoriasis.

In one embodiment, in any one of the methods above, the anti-IL-23A antibody or an antigen binding fragment thereof as disclosed below.

In one embodiment, the IL-23A antagonist is an anti-IL-23p19 antibody or antigen-binding fragment thereof, wherein the antibody or antigen-binding fragment thereof comprises a light chain variable region comprising the amino acid sequence of SEQ ID NO:1 (CDR1-L); the amino acid sequence of SEQ ID NO:2 (CDR2-L); and the amino acid sequence of SEQ ID NO:3 (CDR3-L); and a heavy chain variable region comprising the amino acid sequence of SEQ ID NO: 4, 7, 8 or 9 (CDR1-H); the amino acid sequence of SEQ ID NO:5 (CDR2-H); and the amino acid sequence of SEQ ID NO:6 (CDR3-H).

In one embodiment, the IL-23A antagonist is an anti-IL-23p19 or antigen-binding fragment thereof antibody, wherein the antibody or antigen-binding fragment thereof comprises a light chain variable region comprising the amino acid sequence of SEQ ID NO:1 (CDR1-L); the amino acid sequence of SEQ ID NO:2 (CDR2-L); and the amino acid sequence of SEQ ID NO:3 (CDR3-L); and a heavy chain variable region comprising the amino acid sequence of SEQ ID NO:4 (CDR1-H); the amino acid sequence of SEQ ID NO:5 (CDR2-H); and the amino acid sequence of SEQ ID NO:6 (CDR3-H).

In one embodiment, the IL-23A antagonist is an anti-IL-23p19 or antigen-binding fragment thereof antibody, wherein the antibody or antigen-binding fragment thereof comprises a light chain variable region comprising the amino acid sequence of SEQ ID NO:1 (CDR1-L); the amino acid sequence of SEQ ID NO:2 (CDR2-L); and the amino acid sequence of SEQ ID NO:3 (CDR3-L); and a heavy chain variable region comprising the amino acid sequence of SEQ ID NO:7 (CDR1-H); the amino acid sequence of SEQ ID NO:5 (CDR2-H); and the amino acid sequence of SEQ ID NO:6 (CDR3-H).

In one embodiment, the IL-23A antagonist is an anti-IL-23p19 or antigen-binding fragment thereof antibody, wherein the antibody or antigen-binding fragment thereof comprises a light chain variable region comprising the amino acid sequence of SEQ ID NO:1 (CDR1-L); the amino acid sequence of SEQ ID NO:2 (CDR2-L); and the amino acid sequence of SEQ ID NO:3 (CDR3-L); and a heavy chain variable region comprising the amino acid sequence of SEQ ID NO:8 (CDR1-H); the amino acid sequence of SEQ ID NO:5 (CDR2-H); and the amino acid sequence of SEQ ID NO:6 (CDR3-H).

In one embodiment, the IL-23A antagonist is an anti-IL-23p19 or antigen-binding fragment thereof antibody, wherein the antibody or antigen-binding fragment thereof comprises a light chain variable region comprising the amino acid sequence of SEQ ID NO:1 (CDR1-L); the amino acid sequence of SEQ ID NO:2 (CDR2-L); and the amino acid sequence of SEQ ID NO:3 (CDR3-L); and a heavy chain variable region comprising the amino acid sequence of SEQ ID NO:9 (CDR1-H); the amino acid sequence of SEQ ID NO:5 (CDR2-H); and the amino acid sequence of SEQ ID NO:6 (CDR3-H).

In one embodiment, the IL-23A antagonist is an anti-IL-23p19 antibody or antigen-binding fragment thereof, wherein the antibody or antigen-binding fragment thereof comprises a light chain variable region comprising the amino acid sequence of any one of SEQ ID NO:10, 11, 12 or 13; and a heavy chain variable region comprising the amino acid sequence any one of SEQ ID NO:14, 15, 16 or 17.

In one embodiment, the IL-23A antagonist is an anti-IL-23p19 antibody or antigen-binding fragment thereof, wherein the antibody or antigen-binding fragment thereof comprises a light chain variable region comprising the amino acid sequence of SEQ ID NO:11 and a heavy chain variable region comprising the amino acid sequence SEQ ID NO:14.

In one embodiment, the IL-23A antagonist is an anti-IL-23p19 antibody or antigen-binding fragment thereof, wherein the antibody or antigen-binding fragment thereof comprises a light chain variable region comprising the amino acid sequence of SEQ ID NO:11 and a heavy chain variable region comprising the amino acid sequence SEQ ID NO:15.

In one embodiment, the IL-23A antagonist is an anti-IL-23p19 antibody or antigen-binding fragment thereof, wherein the antibody or antigen-binding fragment thereof comprises a light chain variable region comprising the amino acid sequence of SEQ ID NO:10 and a heavy chain variable region comprising the amino acid sequence SEQ ID NO:14.

In one embodiment, the IL-23A antagonist is an anti-IL-23p19 antibody or antigen-binding fragment thereof, wherein the antibody or antigen-binding fragment thereof comprises a light chain variable region comprising the amino acid sequence of SEQ ID NO:10 and a heavy chain variable region comprising the amino acid sequence SEQ ID NO:15.

In one embodiment, the anti-IL-23p19 antibody is a humanized antibody. In one embodiment, the anti-IL-23p19 antibody is a monoclonal antibody. In one embodiment, the anti-IL-23p19 antibody is a full length antibody. In one embodiment, the anti-IL-23p19 antibody is a humanized monoclonal anti-IL-23p19 antibody, for example a full length humanized monoclonal antibody. In one embodiment, the antigen-binding fragment is a Fab, F(ab)$_2$, or single chain Fv fragment. In one embodiment, the antigen-binding fragment comprises a light chain variable region and a heavy chain variable region.

In one embodiment, the IL-23A antagonist is an antibody comprising the amino acid sequence SEQ ID NO:14 or 15 linked to a human IgG1, IgG2, IgG3, IgG4, IgM, IgA or IgE heavy chain constant region. An antibody comprising the amino acid sequence of SEQ ID NO: 14 or 15 linked to a human IgG1 heavy chain constant region. An antibody comprising the amino acid sequence of SEQ ID NO:10 or 11 linked to a human kappa or lambda light chain constant region. An antibody comprising the amino acid sequence of SEQ ID NO: 10 or 11 linked to a human kappa light chain constant region.

In one embodiment, the IL-23A antagonist is an antibody comprising the amino acid sequence of SEQ ID NO:14 or 15 linked to a human IgG1 heavy chain constant region; and the amino acid sequence of SEQ ID NO: 10 or 11 linked to a human kappa light chain constant region.

In one embodiment, the IL-23A antagonist is a humanized monoclonal anti-IL-23p19 antibody comprising a light chain variable region comprising the amino acid sequence selected from the group consisting of any one of SEQ ID NO:10, 11, 12 and 13 and a heavy chain variable region comprising the amino acid sequence selected from the group consisting of any one of SEQ ID NO:14, 15, 16 and 17.

In one embodiment, the IL-23A antagonist is a humanized monoclonal anti-IL-23p19 antibody comprising a light chain variable region comprising the amino acid sequence of SEQ ID NO:11 and a heavy chain variable region comprising the amino acid sequence SEQ ID NO:14.

In one embodiment, the IL-23A antagonist is a humanized monoclonal anti-IL-23p19 antibody comprising a light chain variable region comprising the amino acid sequence of SEQ ID NO:11 and a heavy chain variable region comprising the amino acid sequence SEQ ID NO:15.

In one embodiment, the IL-23A antagonist is a humanized monoclonal anti-IL-23p19 antibody comprising a light chain variable region comprising the amino acid sequence of SEQ ID NO:10 and a heavy chain variable region comprising the amino acid sequence SEQ ID NO:14.

In one embodiment, the IL-23A antagonist is a humanized monoclonal anti-IL-23p19 antibody comprising a light chain variable region comprising the amino acid sequence of SEQ ID NO:10 and a heavy chain variable region comprising the amino acid sequence SEQ ID NO:15.

In one embodiment, the IL-23A antagonist is a humanized monoclonal anti-IL-23p19 antibody comprising a light chain comprising the amino acid sequence of SEQ ID NO:18 or 21 and a heavy chain comprising the amino acid sequence of SEQ ID NO:19 or 20.

In one embodiment, the IL-23A antagonist is a humanized monoclonal anti-IL-23p19 antibody comprising a light chain comprising the amino acid sequence of SEQ ID NO:18 and a heavy chain comprising the amino acid sequence of SEQ ID NO:19.

In one embodiment, the IL-23A antagonist is a humanized monoclonal anti-IL-23p19 antibody comprising a light chain comprising the amino acid sequence of SEQ ID NO:18 and a heavy chain comprising the amino acid sequence of SEQ ID NO:20.

In one embodiment, the IL-23A antagonist is a humanized monoclonal anti-IL-23p19 antibody comprising a light chain comprising the amino acid sequence of SEQ ID NO:21 and a heavy chain comprising the amino acid sequence of SEQ ID NO:19.

In one embodiment, the IL-23A antagonist is a humanized monoclonal anti-IL-23p19 antibody comprising a light chain comprising the amino acid sequence of SEQ ID NO: 21 and a heavy chain comprising the amino acid sequence of SEQ ID NO: 20.

In one embodiment, the IL-23A antagonist is Antibody A, Antibody B, Antibody C or Antibody D.

In one embodiment, the IL-23A antagonist is an antibody as disclosed in WO2007/005955, WO2007/024846, WO2007/027714, WO2007/076524, WO2008/103432 or WO2012/061448.

BRIEF DESCRIPTION OF THE FIGURES

FIG. 2: Heat Map showing overall decreases in fold change expression (change from Baseline to Week 8) in a cluster of 79 genes from RNA-seq analysis post-treatment with Antibody A versus placebo with each column representing individual patients. FIG. 2A lists the 79 genes, while

DETAILED DESCRIPTION

Figure 1:
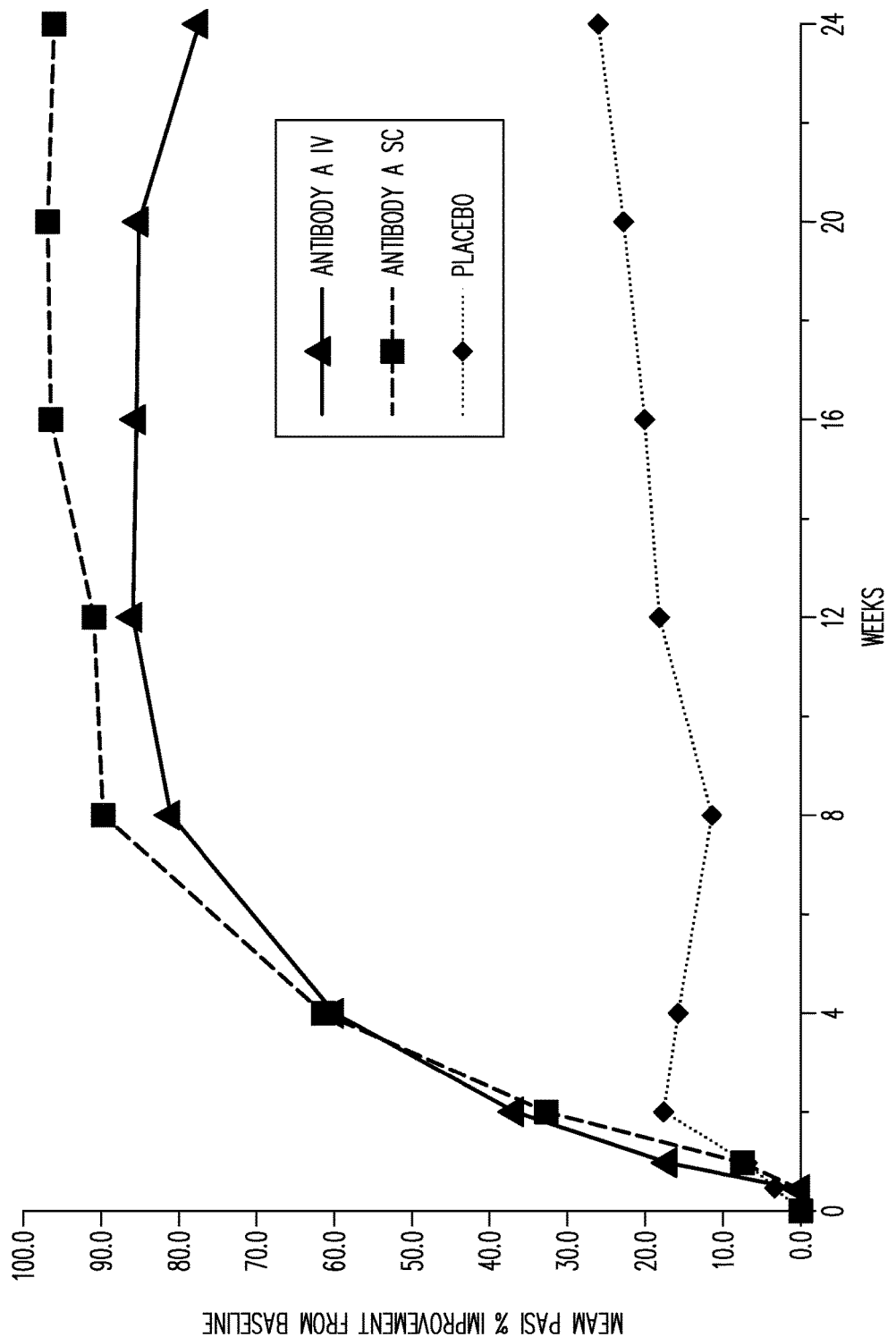
FIG. 1: Mean improvements in PASI score for patients receiving IV or SC Antibody A. For Antibody A IV, N=24 to Week 12 and N=23 thereafter (patient, originally allocated to the Antibody A 5 mg/kg group, lost to follow up due to relocation and discontinued after Week 12). For Antibody A SC, N=15 throughout. IV, intravenous; PASI, psoriasis area severity index; SC, subcutaneous.
Figure 2B:
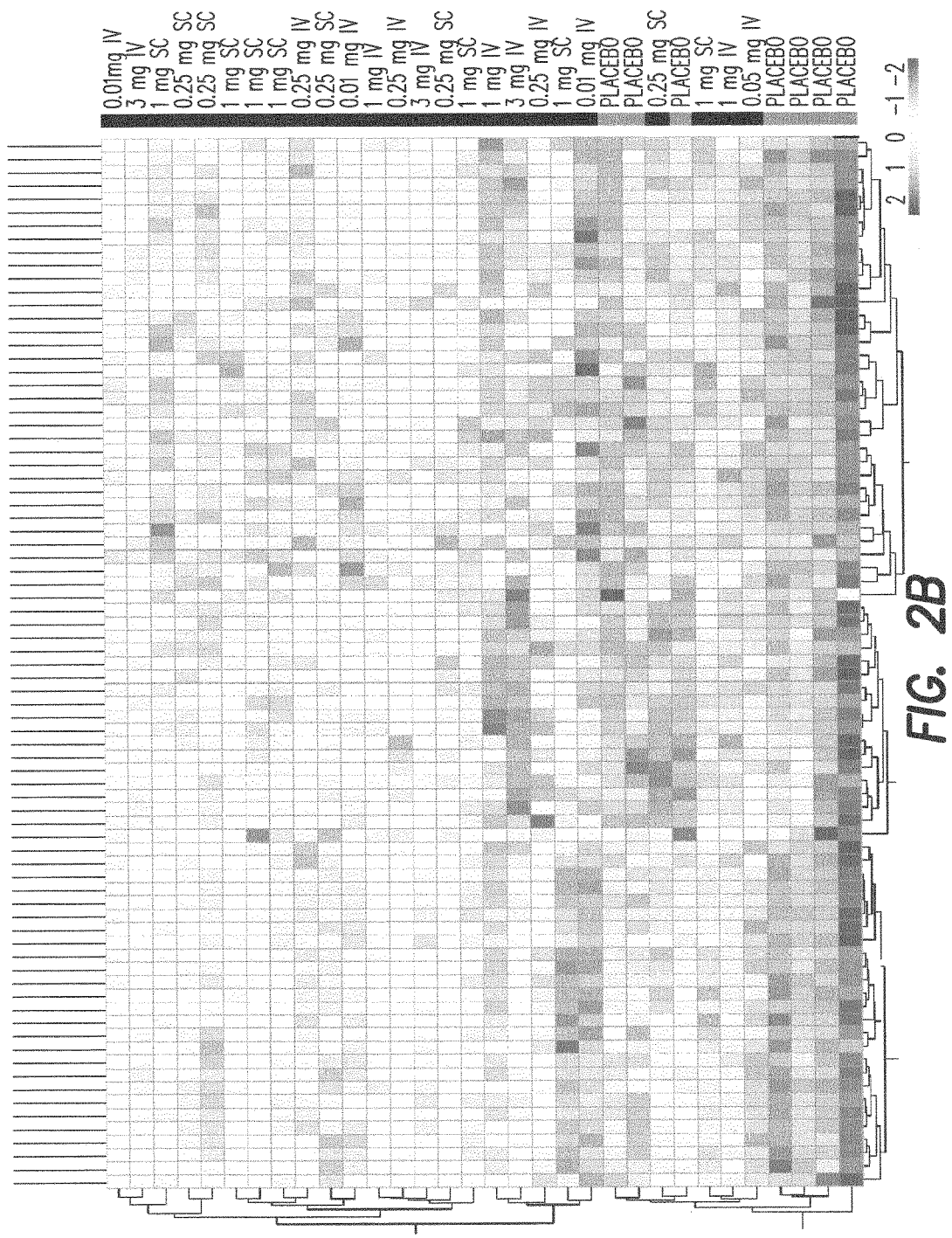
FIG. 2B shows the heat map. The scale shows log 2-fold change in expression of each of the 79 genes with red representing fold-change increase and blue fold-change decrease (Antibody A versus placebo).
Figure 3:
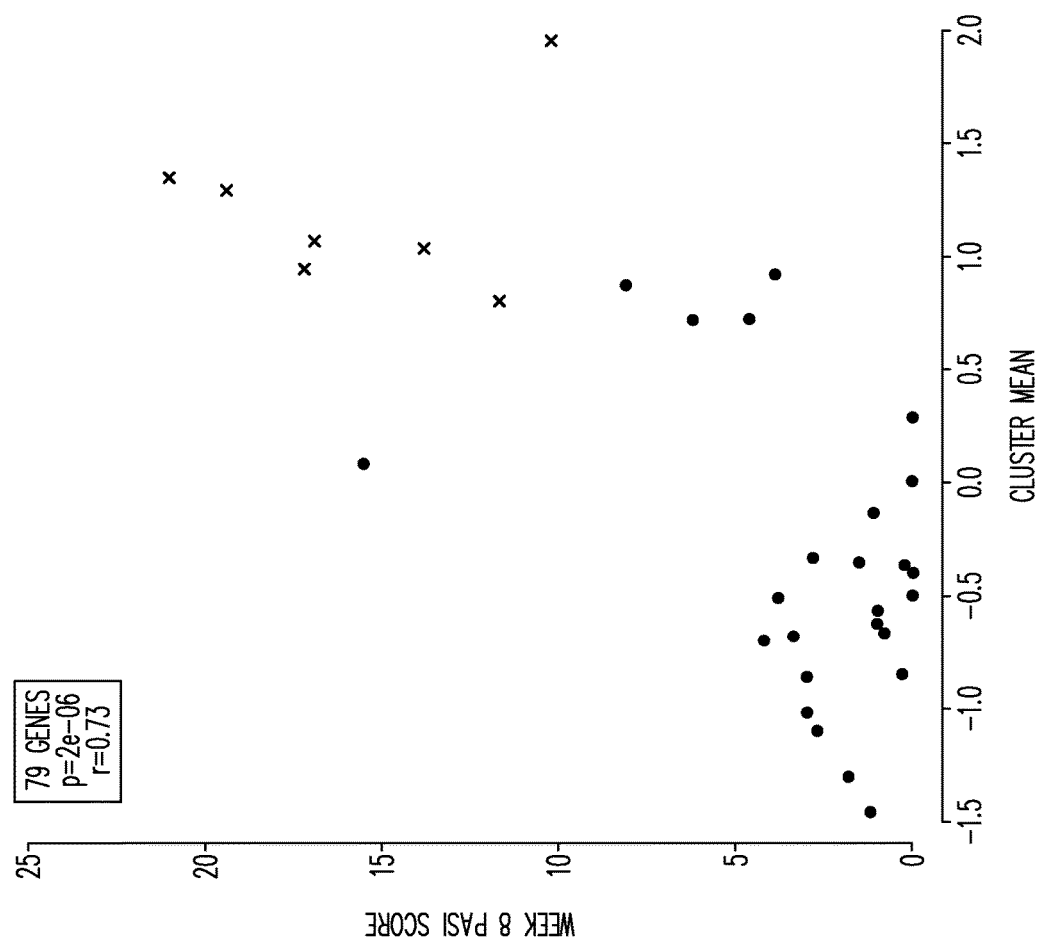
FIG. 3: Correlation plot of the cluster means of the 79 genes (from FIG. 2) for each patient versus PASI scores at Week 8, showing a significant correlation between reductions in expression of this gene cluster in Antibody A treated patients and lower PASI scores [Antibody A (dots) versus placebo (crosses)].

The p19 subunit of IL-23 (also referred to herein as "IL-23A", "IL-23p19" and "p19 subunit") is a 189 amino acid polypeptide containing a 21 aa leader sequence (Oppmann et al. Immunity 13:715 (2000), SEQ ID NO: 22). The biological activity of the molecule is only detected when it is partnered with the IL-12p40 subunit to form IL-23. IL-23 is predominantly expressed by activated dendritic cells (DCs) and phagocytic cells. The receptor for IL-23 was found to be composed of the IL-12Rβ1 subunit of IL-12 receptor partnered with a unique subunit called IL-23R (Parham et al. J. Immunol. 168:5699 (2002)). Expression of the receptor is detected primarily on memory T cells and NK cells. Thus, expression of this cytokine:receptor pair appears to be restricted to specific populations of immune cells. While it was first thought that IL-12 and IL-23 would share many functions, the data has shown the picture to be different. Whereas IL-12 has a predominant role in the production of Th1 cells, IL-23 was found to be critically involved in the production and maintenance of a recently recognized Th cell subset termed Th17 (Kikly et al. Curr. Opin. Immunol. 18:670 (2006), Kastelein et al. Ann. Rev. Immunol. 25:221 (2007)). These cells produce IL-17A, IL-17F, IL-22 and other pro-inflammatory cytokines such as IL-6 and TNF-α. As described below, animal model studies on the role of these Th17 cells show their importance as a driving force in chronic inflammation and autoimmunity.

```
SEQ ID NO: 22:
mlgsravmll lllpwtaqgr avpggsspaw tqcqqlsqkl ctlawsahpl vghmdlreeg deettndvph iqcgdgcdpq glrdnsqfcl qrihqglify ekllgsdift gepsllpdsp vgqlhasllg lsqllqpegh hwetqqipsl spsqpwqrll lrfkilrslq afvavaarvf ahgaatlsp
```

The present invention provides biomarkers useful in the treatment of IL-23A related diseases.

In one embodiment, the present invention provides a method for detecting the presence or absence of a beneficial response in a patient after administration of an IL-23A antagonist, comprising: a) obtaining a biological sample from the patient; b) measuring in said sample the level of expression of one or more biomarkers; c) comparing the level to control value of the level of the biomarkers; and d) determining whether or not the difference in levels between the sample and the control reflects a beneficial response in the patient, wherein the one or more biomarkers are genes/proteins associated with the IL-23/IL-17 axis (for example one or more of IL-23A, IL-23R, IL-22, IL-22RA1 RA2, IL-17A, IL-17F, IL-17RA, and IL-17RC), keratinocyte and epithelial cell differentiation (for example one or more of late cornified envelope protein, transglutaminase 1, and cornifelin), tissue inflammation (for example one or more of β-defensin 2, neutrophil gelatinase lipocalin, and S-100 proteins) or the IFNα pathway (for example one or more of IFIH1, ISG15, IRF7, IFI44, MX1, MX2, STAT1, and TRIM22).

In one embodiment, the presence or absence of a beneficial response in the patient is detected prior to and after administration of the IL-23A antagonist.

In one embodiment, the control value of the value of a patient treated with a placebo. In one embodiment, the control value of the value of a patient treated with a placebo and the difference is the difference between the sample from a patient treated with the IL-23A antagonist and the placebo.

In one embodiment, the level of the gene or the protein of said one or more biomarker is measured. In one embodiment, the patient suffers from psoriasis.

In one embodiment, the control value is calculated using samples from subjects that do not suffer from psoriasis. In one embodiment, the control value, for example the placebo value, is determined using samples from known psoriasis patients, for example from placebo-treated psoriasis patients. In one embodiment, the control value is determined using at least one previous sample taken from the patient.

In one embodiment, the one or more biomarkers is S-100A7, neutrophil gelatinase lipocalin or β-defensin 2. In one embodiment, the biological sample is a skin biopsy, blood, plasma or serum sample. In one embodiment, the IL-23A antagonist is an anti-IL-23A antibody or an antigen binding fragment thereof. In one embodiment, the levels of biomarkers are determined by RNA sequencing or ELISA or another protein assay.

In one embodiment, the method further comprises continuing the administration of the IL-23A antagonist to the patient if the difference in levels between the sample and the control reflects a beneficial response in the patient. In one embodiment, the method further comprises continuing the administration of the IL-23A antagonist to the patient if the difference in levels from a patient treated with the antagonist versus the placebo reflects a beneficial response in the patient.

In a further embodiment, the present invention provides a method of determining whether a potential therapeutic agent is efficacious in the treatment of psoriasis comprising: a) obtaining a first biological sample from a psoriasis patient prior to being treated with the potential therapeutic agent; b) treating the psoriasis patient with the potential therapeutic agent; c) obtaining a second biological sample from the psoriasis patient after being treated with the potential therapeutic agent; d) measuring in said first and second sample the levels of expression of one or more biomarkers; and e) comparing the biomarker levels in the second sample to the levels in the first sample, wherein lower biomarker levels in the second sample than in the first sample indicate that the potential therapeutic agent is efficacious, and further wherein the one or more biomarkers are genes associated with the IL-23/IL-17 axis (for example one or more of IL-23A, IL-23R, IL-22, IL-22RA1 RA2, IL-17A, IL-17F, IL-17RA, and IL-17RC), keratinocyte and epithelial cell differentiation (for example one or more of late cornified envelope protein, transglutaminase 1, and cornifelin), tissue inflammation (for example one or more of β-defensin 2, neutrophil gelatinase lipocalin, and S-100 proteins) and the IFNα pathway (for example one or more of IFIH1, ISG15, IRF7, IFI44, MX1, MX2, STAT1, and TRIM22). In one embodiment, said step e) comprises comparing the biomarker levels in the second sample to the levels in the first sample, wherein lower biomarker levels in the second sample than in the first sample and correlation with improvement in a clinical efficacy measure ie PASI scores in case of Psoriasis indicates the potential therapeutic agent is efficacious.

In one embodiment, the method further comprises continuing the treatment of the patient if biomarker levels in the second sample is lower than the levels in the first sample.

In a further embodiment, the present invention provides a method of treating psoriasis in a subject comprising: a) determining whether to initiate treatment of the subject, modify the treatment dose, modify the dosing interval, or discontinue treatment, based on the method of any of the preceding claims; and b) modifying the treatment regimen based on the determination.

In a further embodiment, the present invention provides a method of monitoring patient response to a psoriasis treatment comprising:
a) obtaining a first biological sample from the patient;
b) measuring the level of one or more biomarkers in said first biological sample, wherein said one or more biomarkers are genes/proteins associated with the IL-23/IL-17 axis (for example one of more of IL-23A, IL-23R, IL-22, IL-22RA1 RA2, IL-17A, IL-17F, IL-17RA, and IL-17RC), keratinocyte and epithelial cell differentiation (for example one or more of late cornified envelope protein, transglutaminase 1, and cornifelin), tissue inflammation (for example one or more of β-defensin 2, neutrophil gelatinase lipocalin, and S-100 proteins) and the IFNα pathway (for example one or more of IFIH1, ISG15, IRF7, IFI44, MX1, MX2, STAT1, and TRIM22);
c) administering a treatment compound to the patient;
d) obtaining a second biological sample from the patient;
e) measuring the level of said one or more biomarkers in said second biological sample; and
f) comparing the levels of the one or more biomarkers obtained from first and second biological samples;
wherein a decreased level of the one or more biomarkers in the second biological sample indicates an effective response. In one aspect, a decreased level of the one or more biomarkers in the second biological sample and correlation with improvement in a clinical efficacy measure ie PASI scores in case of Psoriasis indicates an effective response.

In a further embodiment, the present invention provides a method for monitoring patient compliance with a drug treatment protocol for psoriasis comprising:
a) obtaining a biological sample from said patient;
b) measuring the level of one or more biomarkers, wherein the one or more biomarkers are genes/proteins associated with the IL-23/IL-17 axis (for example one or more of IL-23A, IL-23R, IL-22, IL-22RA1 RA2, IL-17A, IL-17F, IL-17RA, and IL-17RC), keratinocyte and epithelial cell differentiation (for example one of more of late cornified envelope protein, transglutaminase 1, and cornifelin), tissue inflammation (for example one of more of β-defensin 2, neutrophil gelatinase lipocalin, and S-100 proteins) and the IFNα pathway (for example one of more of IFIH1, ISG15, IRF7, IFI44, MX1, MX2, STAT1, and TRIM22); and
c) determining if the level is decreased in the patient sample compared to the level in a control untreated sample;
wherein a decreased level indicates patient compliance with said drug treatment protocol.

In one embodiment, in any one of the methods above, the level of the one or more biomarkers in the second biological sample is decreased by at least about 20%, 25%, 30%, 35%, 40%, 45%, 50%, 55%, 60%, 65%, 65%, 70%, 75%, 80%, 85%, 90%, or 95% or more as compared to the level in the first biological sample.

In one embodiment, in any one of the methods above, the biological sample is a skin biopsy, blood, plasma or serum sample. In one embodiment, in any one of the methods above, the IL-23A antagonist is an anti-IL-23A antibody or an antigen binding fragment thereof. In one embodiment, in any one of the methods above, the levels of biomarkers are determined by RNA sequencing or ELISA or another protein assay.

In one embodiment, the present invention further provides a method of selecting a patient, for example using a method disclosed herein. In one embodiment, the present invention further provides a method of enriching a patient population for patients expected to have a beneficial response after treatment with an IL-23 antagonist, for example using a method of the present invention. In one embodiment, the present invention further provides a method of enriching a patient population for patients expected to have a beneficial response prior to or early after treatment with an IL-23 antagonist, for example using a method of the present invention.

In a further embodiment, the present invention further provides an ELISA kit comprising one or more antibodies or antigen binding fragments thereof that specifically bind to one or more biomarkers, wherein the one or more biomarkers is ieS-100 proteins, neutrophil gelatinase lipocalin or β-defensin 2. In one embodiment, the ELISA or other protein assay kit further comprises instructions for use of the kit prior to treatment or for monitoring psoriasis.

In one embodiment, in any one of the methods above, the anti-IL-23A antibody or an antigen binding fragment thereof as disclosed below.

In one aspect, the anti-IL-23p19 antibody is a humanized antibody. In one aspect, the anti-IL-23p19 antibody is a monoclonal antibody. In one aspect, the anti-IL-23p19 antibody is a full length antibody. In one aspect, the anti-IL-23p19 antibody is a humanized monoclonal antibody, for example a full length humanized monoclonal antibody.

An antibody or antigen-binding fragment thereof of the present invention recognizes specific "IL-23p19 antigen epitope" or "IL-23p19 epitope". As used herein these terms refer to a molecule (e.g., a peptide) or a fragment of a molecule capable of immunoreactivity with an anti-IL-23p19 antibody and, for example, include an IL-23p19 antigenic determinant recognized by the any of the antibodies having a light chain/heavy chain sequence combination of SEQ ID NO:11/14, 11/15, 10/14 or 10/15.

The generalized structure of antibodies or immunoglobulin is well known to those of skill in the art. These molecules are heterotetrameric glycoproteins, typically of about 150,000 daltons, composed of two identical light (L) chains and two identical heavy (H) chains and are typically referred to as full length antibodies. Each light chain is covalently linked to a heavy chain by one disulfide bond to form a heterodimer, and the heterotrameric molecule is formed through a covalent disulfide linkage between the two identical heavy chains of the heterodimers. Although the light and heavy chains are linked together by one disulfide bond, the number of disulfide linkages between the two heavy chains varies by immunoglobulin isotype. Each heavy and light chain also has regularly spaced intrachain disulfide bridges. Each heavy chain has at the amino-terminus a variable domain ($V_H$), followed by three or four constant domains ($C_{H1}$, $C_{H2}$, $C_{H3}$, and $C_{H4}$), as well as a hinge region between $C_{H1}$ and $C_{H2}$. Each light chain has two domains, an amino-terminal variable domain ($V_L$) and a carboxy-terminal constant domain ($C_L$). The $V_L$ domain associates non-covalently with the $V_H$ domain, whereas the $C_L$ domain is commonly covalently linked to the $C_{H1}$ domain via a disulfide bond. Particular amino acid residues are believed to form an interface between the light and heavy chain variable domains (Chothia et al., 1985, J. Mol. Biol. 186:651-663). Variable domains are also referred herein as variable regions.

Certain domains within the variable domains differ extensively between different antibodies i.e., are "hypervariable." These hypervariable domains contain residues that are directly involved in the binding and specificity of each particular antibody for its specific antigenic determinant. Hypervariability, both in the light chain and the heavy chain variable domains, is concentrated in three segments known as complementarity determining regions (CDRs) or hypervariable loops (HVLs). CDRs are defined by sequence comparison in Kabat et al., 1991, In: Sequences of Proteins of Immunological Interest, 5$^{th}$ Ed. Public Health Service, National Institutes of Health, Bethesda, Md., whereas HVLs (also referred herein as CDRs) are structurally defined according to the three-dimensional structure of the variable domain, as described by Chothia and Lesk, 1987, J. Mol. Biol. 196: 901-917. These two methods result in slightly different identifications of a CDR. As defined by Kabat, CDR-L1 is positioned at about residues 24-34, CDR-L2, at about residues 50-56, and CDR-L3, at about residues 89-97 in the light chain variable domain; CDR-H1 is positioned at about residues 31-35, CDR-H2 at about residues 50-65, and CDR-H3 at about residues 95-102 in the heavy chain variable domain. The exact residue numbers that encompass a particular CDR will vary depending on the sequence and size of the CDR. Those skilled in the art can routinely determine which residues comprise a particular CDR given the variable region amino acid sequence of the antibody. The CDR1, CDR2, CDR3 of the heavy and light chains therefore define the unique and functional properties specific for a given antibody.

The three CDRs within each of the heavy and light chains are separated by framework regions (FR), which contain sequences that tend to be less variable. From the amino terminus to the carboxy terminus of the heavy and light chain variable domains, the FRs and CDRs are arranged in the order: FR1, CDR1, FR2, CDR2, FR3, CDR3, and FR4. The largely β-sheet configuration of the FRs brings the CDRs within each of the chains into close proximity to each other as well as to the CDRs from the other chain. The resulting conformation contributes to the antigen binding site (see Kabat et al., 1991, NIH Publ. No. 91-3242, Vol. I, pages 647-669), although not all CDR residues are necessarily directly involved in antigen binding.

FR residues and Ig constant domains are not directly involved in antigen binding, but contribute to antigen binding and/or mediate antibody effector function. Some FR residues are thought to have a significant effect on antigen binding in at least three ways: by noncovalently binding directly to an epitope, by interacting with one or more CDR residues, and by affecting the interface between the heavy and light chains. The constant domains are not directly involved in antigen binding but mediate various Ig effector functions, such as participation of the antibody in antibody dependent cellular cytotoxicity (ADCC), complement dependent cytotoxicity (CDC) and antibody dependent cellular phagocytosis (ADCP).

The light chains of vertebrate immunoglobulins are assigned to one of two clearly distinct classes, kappa (κ) and lambda (λ), based on the amino acid sequence of the constant domain. By comparison, the heavy chains of mammalian immunoglobulins are assigned to one of five major classes, according to the sequence of the constant domains: IgA, IgD, IgE, IgG, and IgM. IgG and IgA are further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, β, ε, γ, and μ, respectively. The subunit structures and three-dimensional configurations of the classes of native immunoglobulins are well known.

The terms, "antibody", "anti-IL-23p19 antibody", "humanized anti-IL-23p19 antibody", "humanized anti-IL-23p19 epitope antibody", and "variant humanized anti-IL-23p19 epitope antibody" specifically encompass monoclonal antibodies (including full length monoclonal antibodies), polyclonal antibodies, multispecific antibodies (e.g., bispecific antibodies), and antibody fragments such as variable domains and other portions of antibodies that exhibit a desired biological activity, e.g., IL-23p19 binding. The term "monoclonal antibody" (mAb) refers to an antibody that is highly specific, being directed against a single antigenic determinant, an "epitope". Therefore, the modifier "monoclonal" is indicative of antibodies directed to the identical epitope and is not to be construed as requiring production of the antibody by any particular method. It should be understood that monoclonal antibodies can be made by any technique or methodology known in the art; including e.g., the hybridoma method (Kohler et al., 1975, Nature 256: 495), or recombinant DNA methods known in the art (see, e.g., U.S. Pat. No. 4,816,567), or methods of isolation of monoclonal recombinantly produced using phage antibody libraries, using techniques described in Clackson et al., 1991, Nature 352: 624-628, and Marks et al., 1991, J. Mol. Biol. 222: 581-597.

The term "monomer" refers to a homogenous form of an antibody. For example, for a full-length antibody, monomer means a monomeric antibody having two identical heavy chains and two identical light chains.

Chimeric antibodies consist of the heavy and light chain variable regions of an antibody from one species (e.g., a non-human mammal such as a mouse) and the heavy and light chain constant regions of another species (e.g., human) antibody and can be obtained by linking the DNA sequences encoding the variable regions of the antibody from the first species (e.g., mouse) to the DNA sequences for the constant regions of the antibody from the second (e.g. human) species and transforming a host with an expression vector containing the linked sequences to allow it to produce a chimeric antibody. Alternatively, the chimeric antibody also could be one in which one or more regions or domains of the heavy and/or light chain is identical with, homologous to, or a variant of the corresponding sequence in a monoclonal antibody from another immunoglobulin class or isotype, or from a consensus or germline sequence. Chimeric antibodies can include fragments of such antibodies, provided that the antibody fragment exhibits the desired biological activity of its parent antibody, for example binding to the same epitope (see, e.g., U.S. Pat. No. 4,816,567; and Morrison et al., 1984, Proc. Natl. Acad. Sci. USA 81: 6851-6855).

The terms, "antibody fragment", "anti-IL-23p19 antibody fragment", "anti-IL-23p19 epitope antibody fragment", "humanized anti-IL-23p19 antibody fragment", "humanized anti-IL-23p19 epitope antibody fragment", "variant humanized anti-IL-23p19 epitope antibody fragment" refer to a portion of a full length anti-IL-23p19 antibody, in which a variable region or a functional capability is retained, for example, specific IL-23p19 epitope binding. Examples of antibody fragments include, but are not limited to, a Fab, Fab', F(ab')$_2$, Fd, Fv, scFv and scFv-Fc fragment, a diabody, a linear antibody, a single-chain antibody, a minibody, a diabody formed from antibody fragments, and multispecific antibodies formed from antibody fragments.

Full length antibodies can be treated with enzymes such as papain or pepsin to generate useful antibody fragments. Papain digestion is used to produces two identical antigen-binding antibody fragments called "Fab" fragments, each with a single antigen-binding site, and a residual "Fc" fragment. The Fab fragment also contains the constant domain of the light chain and the $C_{H1}$ domain of the heavy chain. Pepsin treatment yields a F(ab')$_2$ fragment that has two antigen-binding sites and is still capable of cross-linking antigen.

Fab' fragments differ from Fab fragments by the presence of additional residues including one or more cysteines from the antibody hinge region at the C-terminus of the $C_{H1}$ domain. F(ab')$_2$ antibody fragments are pairs of Fab' fragments linked by cysteine residues in the hinge region. Other chemical couplings of antibody fragments are also known.

"Fv" fragment contains a complete antigen-recognition and binding site consisting of a dimer of one heavy and one light chain variable domain in tight, non-covalent association. In this configuration, the three CDRs of each variable domain interact to define an antigen-biding site on the surface of the $V_H$-$V_L$ dimer. Collectively, the six CDRs confer antigen-binding specificity to the antibody.

A "single-chain Fv" or "scFv" antibody fragment is a single chain Fv variant comprising the $V_H$ and $V_L$ domains of an antibody where the domains are present in a single polypeptide chain. The single chain Fv is capable of recognizing and binding antigen. The scFv polypeptide may optionally also contain a polypeptide linker positioned between the $V_H$ and $V_L$ domains in order to facilitate formation of a desired three-dimensional structure for antigen binding by the scFv (see, e.g., Pluckthun, 1994, In The Pharmacology of monoclonal Antibodies, Vol. 113, Rosenburg and Moore eds., Springer-Verlag, New York, pp. 269-315).

A "diabody" refers to small antibody fragments with two antigen-binding sites, which fragments comprise a heavy chain variable domain (V.sub.H) connected to a light chain variable domain (V.sub.L) in the same polypeptide chain (V.sub.H-V.sub.L or V.sub.L-V.sub.H). Diabodies are described more fully in, e.g., Holliger et al. (1993) Proc. Natl. Acad. Sci. USA 90: 6444-6448.

Other recognized antibody fragments include those that comprise a pair of tandem Fd segments ($V_H$-$C_{H1}$-$V_H$-$C_{H1}$) to form a pair of antigen binding regions. These "linear antibodies" can be bispecific or monospecific as described in, for example, Zapata et al. 1995, Protein Eng. 8(10):1057-1062.

A "humanized antibody" or a "humanized antibody fragment" is a specific type of chimeric antibody which includes an immunoglobulin amino acid sequence variant, or fragment thereof, which is capable of binding to a predetermined antigen and which, comprises one or more FRs having substantially the amino acid sequence of a human immunoglobulin and one or more CDRs having substantially the amino acid sequence of a non-human immunoglobulin. This non-human amino acid sequence often referred to as an "import" sequence is typically taken from an "import" antibody domain, particularly a variable domain. In general, a humanized antibody includes at least the CDRs or HVLs of a non-human antibody, inserted between the FRs of a human heavy or light chain variable domain. The present invention describes specific humanized anti-IL-23p19 antibodies which contain CDRs derived from the mouse monoclonal antibodies or humanized CDRs shown in Tables 1 and 2 inserted between the FRs of human germline sequence heavy and light chain variable domains. It will be understood that certain mouse FR residues may be important to the function of the humanized antibodies and therefore certain of the human germline sequence heavy and light chain variable domains residues are modified to be the same as those of the corresponding mouse sequence.

In another aspect, a humanized anti-IL-23p19 antibody comprises substantially all of at least one, and typically two, variable domains (such as contained, for example, in Fab, Fab', F(ab')2, Fabc, and Fv fragments) in which all, or substantially all, of the CDRs correspond to those of a non-human immunoglobulin, and specifically herein, all of the CDRs are mouse or humanized sequences as detailed in Tables 1 and 2 herein below and all, or substantially all, of the FRs are those of a human immunoglobulin consensus or germline sequence. In another aspect, a humanized anti-IL-23p19 antibody also includes at least a portion of an immunoglobulin Fc region, typically that of a human immunoglobulin. Ordinarily, the antibody will contain both the light chain as well as at least the variable domain of a heavy chain. The antibody also may include one or more of the $C_{H1}$, hinge, $C_{H2}$, $C_{H3}$, and/or $C_{H4}$ regions of the heavy chain, as appropriate.

A humanized anti-IL-23p19 antibody can be selected from any class of immunoglobulins, including IgM, IgG, IgD, IgA and IgE, and any isotype, including $IgG_1$, $IgG_2$, $IgG_3$, $IgG_4$, $IgA_1$ and $IgA_2$. For example, the constant domain can be a complement fixing constant domain where it is desired that the humanized antibody exhibit cytotoxic activity, and the isotype is typically $IgG_1$. Where such cytotoxic activity is not desirable, the constant domain may be of another isotype, e.g., IgG$_2$. An alternative humanized anti-IL-23p19 antibody can comprise sequences from more than one immunoglobulin class or isotype, and selecting particular constant domains to optimize desired effector functions is within the ordinary skill in the art. In specific embodiments, the present invention provides antibodies that are IgG1 antibodies and more particularly, are IgG1 antibodies in which there is a knock-out of effector functions.

The FRs and CDRs, or HVLs, of a humanized anti-IL-23p19 antibody need not correspond precisely to the parental sequences. For example, one or more residues in the import CDR, or HVL, or the consensus or germline FR sequence may be altered (e.g., mutagenized) by substitution, insertion or deletion such that the resulting amino acid residue is no longer identical to the original residue in the corresponding position in either parental sequence but the antibody nevertheless retains the function of binding to IL-23p19. Such alteration typically will not be extensive and will be conservative alterations. Usually, at least 75% of the humanized antibody residues will correspond to those of the parental consensus or germline FR and import CDR sequences, more often at least 90%, and most frequently greater than 95%, or greater than 98% or greater than 99%.

Immunoglobulin residues that affect the interface between heavy and light chain variable regions ("the V$_L$-V$_H$ interface") are those that affect the proximity or orientation of the two chains with respect to one another. Certain residues that may be involved in interchain interactions include V$_L$ residues 34, 36, 38, 44, 46, 87, 89, 91, 96, and 98 and V$_H$ residues 35, 37, 39, 45, 47, 91, 93, 95, 100, and 103 (utilizing the numbering system set forth in Kabat et al., Sequences of Proteins of Immunological Interest (National Institutes of Health, Bethesda, Md., 1987)). U.S. Pat. No. 6,407,213 also discusses that residues such as V$_L$ residues 43 and 85, and V$_H$ residues 43 and 60 also may be involved in this interaction. While these residues are indicated for human IgG only, they are applicable across species. Important antibody residues that are reasonably expected to be involved in interchain interactions are selected for substitution into the consensus sequence.

The terms "consensus sequence" and "consensus antibody" refer to an amino acid sequence which comprises the most frequently occurring amino acid residue at each location in all immunoglobulins of any particular class, isotype, or subunit structure, e.g., a human immunoglobulin variable domain. The consensus sequence may be based on immunoglobulins of a particular species or of many species. A "consensus" sequence, structure, or antibody is understood to encompass a consensus human sequence as described in certain embodiments, and to refer to an amino acid sequence which comprises the most frequently occurring amino acid residues at each location in all human immunoglobulins of any particular class, isotype, or subunit structure. Thus, the consensus sequence contains an amino acid sequence having at each position an amino acid that is present in one or more known immunoglobulins, but which may not exactly duplicate the entire amino acid sequence of any single immunoglobulin. The variable region consensus sequence is not obtained from any naturally produced antibody or immunoglobulin. Kabat et al., 1991, Sequences of Proteins of Immunological Interest, 5th Ed. Public Health Service, National Institutes of Health, Bethesda, Md., and variants thereof. The FRs of heavy and light chain consensus sequences, and variants thereof, provide useful sequences for the preparation of humanized anti-IL-23p19 antibodies. See, for example, U.S. Pat. Nos. 6,037,454 and 6,054,297.

Human germline sequences are found naturally in the human population. A combination of those germline genes generates antibody diversity. Germline antibody sequences for the light chain of the antibody come from conserved human germline kappa or lambda v-genes and j-genes. Similarly the heavy chain sequences come from germline v-, d- and j-genes (LeFranc, M-P, and LeFranc, G, "The Immunoglobulin Facts Book" Academic Press, 2001).

As used herein, "variant", "anti-IL-23p19 variant", "humanized anti-IL-23p19 variant", or "variant humanized anti-IL-23p19" each refers to a humanized anti-IL-23p19 antibody having at least a light chain variable murine CDR from any of the sequences as shown in Table 1 or a heavy chain murine CDR sequence derived from the murine monoclonal antibody as shown in Table 2. Variants include those having one or more amino acid changes in one or both light chain or heavy chain variable domains, provided that the amino acid change does not substantially impair binding of the antibody to IL-23p19. Exemplary humanized antibodies produced herein include those designated as Antibody A, Antibody B, Antibody C and Antibody D, and the various light chains and heavy chains of the same are shown in SEQ ID Nos:18 and 21, and SEQ ID Nos:19 and 20, respectively.

An "isolated" antibody is one that has been identified and separated and/or recovered from a component of its natural environment. Contaminant components of the antibody's natural environment are those materials that may interfere with diagnostic or therapeutic uses of the antibody, and can be enzymes, hormones, or other proteinaceous or nonproteinaceous solutes. In one aspect, the antibody will be purified to at least greater than 95% isolation by weight of antibody.

An isolated antibody includes an antibody in situ within recombinant cells in which it is produced, since at least one component of the antibody's natural environment will not be present. Ordinarily however, an isolated antibody will be prepared by at least one purification step in which the recombinant cellular material is removed.

The term "antibody performance" refers to factors that contribute to antibody recognition of antigen or the effectiveness of an antibody in vivo. Changes in the amino acid sequence of an antibody can affect antibody properties such as folding, and can influence physical factors such as initial rate of antibody binding to antigen (k$_a$), dissociation constant of the antibody from antigen (k$_d$), affinity constant of the antibody for the antigen (Kd), conformation of the antibody, protein stability, and half life of the antibody.

The term "epitope tagged" when used herein, refers to an anti-IL-23p19 antibody fused to an "epitope tag". An "epitope tag" is a polypeptide having a sufficient number of amino acids to provide an epitope for antibody production, yet is designed such that it does not interfere with the desired activity of the humanized anti-IL-23p19 antibody. The epitope tag is usually sufficiently unique such that an antibody raised against the epitope tag does not substantially cross-react with other epitopes. Suitable tag polypeptides generally contain at least 6 amino acid residues and usually contain about 8 to 50 amino acid residues, or about 9 to 30 residues. Examples of epitope tags and the antibody that binds the epitope include the flu HA tag polypeptide and its antibody 12CA5 (Field et al., 1988 Mol. Cell. Biol. 8: 2159-2165; c-myc tag and 8F9, 3C7, 6E10, G4, B7 and 9E10 antibodies thereto (Evan et al., 1985, Mol. Cell. Biol. 5(12):3610-3616; and Herpes simplex virus glycoprotein D (gD) tag and its antibody (Paborsky et al. 1990, Protein Engineering 3(6): 547-553). In certain embodiments, the epitope tag is a "salvage receptor binding epitope". As used herein, the term "salvage receptor binding epitope" refers to an epitope of the Fc region of an IgG molecule (such as IgG$_1$, IgG$_2$, IgG$_3$, or IgG$_4$) that is responsible for increasing the in vivo serum half-life of the IgG molecule.

For diagnostic as well as therapeutic monitoring purposes, the antibodies of the invention also may be conjugated to a label, either a label alone or a label and an additional second agent (prodrug, chemotherapeutic agent and the like). A label, as distinguished from the other second agents refers to an agent that is a detectable compound or composition and it may be conjugated directly or indirectly to a humanized antibody of the present invention. The label may itself be detectable (e.g., radioisotope labels or fluorescent labels) or, in the case of an enzymatic label, may catalyze chemical alteration of a substrate compound or composition that is detectable. Labeled humanized anti-IL-23p19 antibody can be prepared and used in various applications including in vitro and in vivo diagnostics.

In various aspects of the present invention one or more domains of the humanized antibodies will be recombinantly expressed. Such recombinant expression may employ one or more control sequences, i.e., polynucleotide sequences necessary for expression of an operably linked coding sequence in a particular host organism. The control sequences suitable for use in prokaryotic cells include, for example, promoter, operator, and ribosome binding site sequences. Eukaryotic control sequences include, but are not limited to, promoters, polyadenylation signals, and enhancers. These control sequences can be utilized for expression and production of humanized anti-IL-23p19 antibody in prokaryotic and eukaryotic host cells.

A nucleic acid sequence is "operably linked" when it is placed into a functional relationship with another nucleic acid sequence. For example, a nucleic acid presequence or secretory leader is operably linked to a nucleic acid encoding a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers are optionally contiguous. Linking can be accomplished by ligation at convenient restriction sites. If such sites do not exist, synthetic oligonucleotide adaptors or linkers can be used.

As used herein, the expressions "cell", "cell line", and "cell culture" are used interchangeably and all such designations include the progeny thereof. Thus, "transformants" and "transformed cells" include the primary subject cell and cultures derived therefrom without regard for the number of transfers.

The term "mammal" for purposes of treatment refers to any animal classified as a mammal, including humans, domesticated and farm animals, and zoo, sports, or pet animals, such as dogs, horses, cats, cows, and the like. Preferably, the mammal is human.

A "disorder", as used herein, is any condition that would benefit from treatment with a humanized anti-IL-23p19 antibody described herein. This includes chronic and acute disorders or diseases including those pathological conditions that predispose the mammal to the disorder in question.

As used herein, the term "IL-23-associated disorder" or "IL-23-associated disease" refers to a condition in which IL-23 activity contributes to the disease and typically where IL-23 is abnormally expressed. An IL-23-associated disorder includes diseases and disorders of the immune system, such as autoimmune disorders and inflammatory disorders. Such conditions include psoriasis, inflammatory bowel disease, for example ulcerative colitis or Crohn's disease, and spondyloarthritis, for example ankylosing spondylitis, non-radiographic axial spondyloarthritis, peripheral spondyloarthritis or psoriatic arthritis.

The term "intravenous infusion" refers to introduction of an agent into the vein of an animal or human patient over a period of time greater than approximately 15 minutes, generally between approximately 30 to 90 minutes.

The term "intravenous bolus" or "intravenous push" refers to drug administration into a vein of an animal or human such that the body receives the drug in approximately 15 minutes or less, generally 5 minutes or less.

The term "subcutaneous administration" refers to introduction of an agent under the skin of an animal or human patient, preferable within a pocket between the skin and underlying tissue, by relatively slow, sustained delivery from a drug receptacle. Pinching or drawing the skin up and away from underlying tissue may create the pocket.

The term "subcutaneous infusion" refers to introduction of a drug under the skin of an animal or human patient, preferably within a pocket between the skin and underlying tissue, by relatively slow, sustained delivery from a drug receptacle for a period of time including, but not limited to, 30 minutes or less, or 90 minutes or less. Optionally, the infusion may be made by subcutaneous implantation of a drug delivery pump implanted under the skin of the animal or human patient, wherein the pump delivers a predetermined amount of drug for a predetermined period of time, such as 30 minutes, 90 minutes, or a time period spanning the length of the treatment regimen.

The term "subcutaneous bolus" refers to drug administration beneath the skin of an animal or human patient, where bolus drug delivery is less than approximately 15 minutes; in another aspect, less than 5 minutes, and in still another aspect, less than 60 seconds. In yet even another aspect, administration is within a pocket between the skin and underlying tissue, where the pocket may be created by pinching or drawing the skin up and away from underlying tissue.

The term "therapeutically effective amount" is used to refer to an amount of an active agent that relieves or ameliorates one or more of the symptoms of the disorder being treated. In another aspect, the therapeutically effective amount refers to a target serum concentration that has been shown to be effective in, for example, slowing disease progression. Efficacy can be measured in conventional ways, depending on the condition to be treated.

The terms "treatment" and "therapy" and the like, as used herein, are meant to include therapeutic as well as prophylactic, or suppressive measures for a disease or disorder leading to any clinically desirable or beneficial effect, including but not limited to alleviation or relief of one or more symptoms, regression, slowing or cessation of progression of the disease or disorder. Thus, for example, the term treatment includes the administration of an agent prior to or following the onset of a symptom of a disease or disorder thereby preventing or removing one or more signs of the disease or disorder. As another example, the term includes the administration of an agent after clinical manifestation of the disease to combat the symptoms of the disease. Further, administration of an agent after onset and after clinical symptoms have developed where administration affects clinical parameters of the disease or disorder, such as the degree of tissue injury or the amount or extent of metastasis, whether or not the treatment leads to amelioration of the disease, comprises "treatment" or "therapy" as used herein. Moreover, as long as the compositions of the invention either alone or in combination with another therapeutic agent alleviate or ameliorate at least one symptom of a disorder being treated as compared to that symptom in the absence of use of the humanized anti-IL-23p19 antibody composition, the result should be considered an effective treatment of the underlying disorder regardless of whether all the symptoms of the disorder are alleviated or not.

The term "package insert" is used to refer to instructions customarily included in commercial packages of therapeutic products, that contain information about the indications, usage, administration, contraindications and/or warnings concerning the use of such therapeutic products.

Antibodies

The CDRs of selected antibodies used in the context of the present invention are shown in Table 1 and 2. The variable regions of selected antibodies used in the context of the present invention are shown in Table 3 and 4.

TABLE 1

LIGHT CHAIN CDR sequences

| | L-CDR1 | L-CDR2 | L-CDR3 |
|---|---|---|---|
| 6B8 | KASRDVAIAVA (SEQ ID NO: 1) | WASTRHT (SEQ ID NO: 2) | HQYSSYPFT (SEQ ID NO: 3) |

TABLE 2

HEAVY CHAIN CDR sequences

| | H-CDR1 | H-CDR2 | H-CDR3 |
|---|---|---|---|
| 6B8 | GNTFTDQTIH (SEQ ID NO: 4) | YIYPRDDSPKYNENFKG (SEQ ID NO: 5) | PDRSGYAWFIY (SEQ ID NO: 6) |
| Hu_6138-2 | GYTFTDQTIH (SEQ ID NO: 7) | YIYPRDDSPKYNENFKG (SEQ ID NO: 5) | PDRSGYAWFIY (SEQ ID NO: 6) |
| Hu_6138-5 | GFTFTDQTIH (SEQ ID NO: 8) | YIYPRDDSPKYNENFKG (SEQ ID NO: 5) | PDRSGYAWFIY (SEQ ID NO: 6) |
| Hu_6138-36/65 | GGTFTDQTIH (SEQ ID NO: 9) | YIYPRDDSPKYNENFKG (SEQ ID NO: 5) | PDRSGYAWFIY (SEQ ID NO: 6) |

TABLE 3

Humanized 6B8-VK Sequences

| 6B8CVK-65 | DIQMTQSPSSLSASVGDRVTITCKASRDVAIAVAWY QQKPGKVPKLLLLFWASTRHTGVPDRFSGSGSRTDFT LTISSLQPEDLADYYCHQYSSYPFTFGQGTKLEIK (SEQ ID NO: 10) |
|---|---|
| 6B8CVK-66 | DIQMTQSPSSLSASVGDRVTITCKASRDVAIAVAWY QQKPGKVPKLLIYWASTRHTGVPSRFSGSGSRTDFT LTISSLQPEDVADYFCHQYSSYPFTFGSGTKLEIK (SEQ ID NO: 11) |
| 6B8CVK-67 | DIQMTQSPSSLSASVGDRVTITCKASRDVAIAVAWY QQKPGKVPKLLLYWASTRHTGVPSRFSGSGSRTDFT LTISSLQPEDVATYYCHQYSSYPFTFGSGTKLEIK (SEQ ID NO: 12) |

TABLE 3-continued

Humanized 6B8-VK Sequences

| 6B8CVK-78 | DIQMTQSPSSLSASVGDRVTITCKASRDVAIAVAWY QQKPGKVPKLLLLFWASTRHTGVPDRFSGSGSRTDFT LTISSLQPEDLADYYCHQYSSYPFTFGSGTKLEIK (SEQ ID NO: 13) |
|---|---|

TABLE 4

Humanized 6B8-VH Sequence

| 6B8CVH-02 | QVQLVQSGAEVKKPGSSVKVSCKASGYTFTDQTIHW MRQAPGQGLEWIGYIYPRDDSPKYNENFKGKVTITA DKSTSTAYMELSSLRSEDTAVYYCAIPDRSGYAWFI YWGQGTLVTVSS (SEQ ID NO: 14) |
|---|---|
| 6B8CVH-05 | QVQLVQSGAEVKKPGSSVKVSCKASGFTFTDQTIHW VRQAPGQGLEWMGYIYPRDDSPKYNENFKGKVTLTA DKSTSTAYMELSSLRSEDTAVYYCAIPDRSGYAWFI YWGQGTLVTVSS (SEQ ID NO: 15) |
| 6B8CVH-36 | QVQLVQSGAEVKKPGSSVKTSCKASGGTFTDQTIHW VRQRPGQGLEWMGYIYPRDDSPKYNENFKGRVTITA DKSTSTAYMELSSLRSEDTAVYYCAIPDRSGYAWFI YWGQGTLVTVSS (SEQ ID NO: 16) |
| 6B8CVH-65 | QVQLVQSGAEVKKPGSSVKVSCKASGGTFTDQTIHW VRQAPGQGLEWMGYIYPRDDSPKYNENFKGRVTLTA DKSTSTAYMELSSLRSEDTAVYFCARPDRSGYAWFI YWGQGTLVTVSS (SEQ ID NO: 17) |

Selected combination of humanized light chain and heavy chain variable regions derived from mouse antibody 6B8 resulted in Antibodies A, B, C and D:

Antibody A: 6B8-IgG1 KO-2 with IgK-66 (heavy chain variable region 6B8CVH-02 and light chain variable region 6B8CVK-66);

Antibody B: 6B8-IgG1 KO-5 with IgK-66 (heavy chain variable region 6B8CVH-05 and light chain variable region 6B8CVK-66);

Antibody C: 6B8-IgG1 KO-2 with IgK-65 (heavy chain variable region 6B8CVH-02 and light chain variable region 6B8CVK-65);

Antibody D: 6B8-IgG1 KO-5 with IgK-65 (heavy chain variable region 6B8CVH-05 and light chain variable region 6B8CVK-65).

Antibodies A, B, C and D have the heavy and light chain sequences shown in Table 5.

TABLE 5

Heavy and Light Chain DNA and Amino Acid Sequences for Antibodies A, B, C, and D

| Antibody A | IgK light Chain #66 | DIQMTQSPSSLSASVGDRVTITCKASRDVAIAVAWYQ QKPGKVPKLLIYWASTRHTGVPSRFSGSGSRTDFTLT ISSLQPEDVADYFCHQYSSYPFTFGSGTKLEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC (SEQ ID NO: 18) |
|---|---|---|
| | IgG1KO Heavy Chain #2 | QVQLVQSGAEVKKPGSSVKVSCKASGYTFTDQTIHWM RQAPGQGLEWIGYIYPRDDSPKYNENFKGKVTITADK STSTAYMELSSLRSEDTAVYYCAIPDRSGYAWFIYWG QGTLVTVSSASTKGPSVFPLAPSSKSTSGGTAALGCL VKDYFPEPVTVSWNSGALTSGVHTFPAVLQSSGLYSL SSVVTVPSSSLGTQTYICNVNHKPSNTKVDKRVEPKS CDKTHTCPPCPAPEAAGGPSVFLFPPKPKDTLMISRT PEVTCVVVDVSHEDPEVKFNWYVDGVEVHNAKTKPRE EQYNSTYRVVSVLTVLHQDWLNGKEYKCKVSNKALPA PIEKTISKAKGQPREPQVYTLPPSREEMTKNQVSLTC |

TABLE 5-continued

Heavy and Light Chain DNA and Amino Acid Sequences for Antibodies A, B, C, and D

| | | |
|---|---|---|
| | | LVKGFYPSDIAVEWESNGQPENNYKTTPPVLDSDGSF<br>FLYSKLTVDKSRWQQGNVFSCSVMHEALHNHYTQKSL<br>SLSPG (SEQ ID NO: 19) |
| Anti-<br>body<br>B | IgK<br>light<br>Chain<br>#66 | (SEQ ID NO: 18) |
| | IgG1KO<br>Heavy<br>Chain<br>#5 | QVQLVQSGAEVKKPGSSVKVSCKASGFTFTDQTIHWV<br>RQAPGQGLEWMGYIYPRDDSPKYNENFKGKVTLTADK<br>STSTAYMELSSLRSEDTAVYYCAIPDRSGYAWFIYWG<br>QGTLVTVSSASTKGPSVFPLAPSSKSTSGGTAALGCL<br>VKDYFPEPVTVSWNSGALTSGVHTFPAVLQSSGLYSL<br>SSVVTVPSSSLGTQTYICNVNHKPSNTKVDKRVEPKS<br>CDKTHTCPPCPAPEAAGGPSVFLFPPKPKDTLMISRT<br>PEVTCVVVDVSHEDPEVKFNWYVDGVEVHNAKTKPRE<br>EQYNSTYRVVSVLTVLHQDWLNGKEYKCKVSNKALPA<br>PIEKTISKAKGQPREPQVYTLPPSREEMTKNQVSLTC<br>LVKGFYPSDIAVEWESNGQPENNYKTTPPVLDSDGSF<br>FLYSKLTVDKSRWQQGNVFSCSVMHEALHNHYTQKSL<br>SLSPG (SEQ ID NO: 20) |
| Anti-<br>body<br>C | IgK<br>light<br>Chain<br>#65 | DIQMTQSPSSLSASVGDRVTITCKASRDVAIAVAWYQ<br>QKPGKVPKLLLFWASTRHTGVPDRFSGSGSGTDFTLT<br>ISSLQPEDLADYYCHQYSSYPFTFGQGTKLEIKRTVA<br>APSVFIFPPSDEQLKSGTASVVCLLNNFYPREAKVQW<br>KVDNALQSGNSQESVTEQDSKDSTYSLSSTLTLSKAD<br>YEKHKVYACEVTHQGLSSPVTKSFNRGEC (SEQ ID<br>NO: 21) |
| | IgG1KO<br>Heavy<br>Chain<br>#2 | (SEQ ID NO: 19) |
| Anti-<br>body<br>D | IgK<br>light<br>Chain<br>#65 | (SEQ ID NO: 21) |
| | IgG1KO<br>Heavy<br>Chain<br>#5 | (SEQ ID NO: 20) |

Light chains and heavy chain variable regions of Antibodies A, B, C, and D are underlined in Table 5 above.

In one aspect, a humanized antibody of the present invention is Antibody A, Antibody B, Antibody C or Antibody D. Accordingly, in one embodiment, a humanized antibody of the present invention comprises the light chain sequence of SEQ ID NO:18 and the heavy chain sequence of SEQ ID NO:19 (Antibody A). In another embodiment, a humanized antibody of the present invention comprises the light chain sequence of SEQ ID NO:18 and the heavy chain sequence of SEQ ID NO:20 (Antibody B). In another embodiment, a humanized antibody of the present invention comprises the light chain sequence of SEQ ID NO:21 and the heavy chain sequence of SEQ ID NO:19 (Antibody C). In another embodiment, a humanized antibody of the present invention comprises the light chain sequence of SEQ ID NO:21 and the heavy chain sequence of SEQ ID NO:20 (Antibody D).

In a further embodiment, a humanized antibody of the present invention consists of the light chain sequence of SEQ ID NO:18 and the heavy chain sequence of SEQ ID NO:19 (Antibody A). In a further embodiment, a humanized antibody of the present invention consists of the light chain sequence of SEQ ID NO:18 and the heavy chain sequence of SEQ ID NO:20 (Antibody B). In a further embodiment, a humanized antibody of the present invention consists of the light chain sequence of SEQ ID NO:21 and the heavy chain sequence of SEQ ID NO:19 (Antibody C). In a further embodiment, a humanized antibody of the present invention consists of the light chain sequence of SEQ ID NO:21 and the heavy chain sequence of SEQ ID NO:20 (Antibody D).

In some embodiments, the humanized anti-IL-23p19 antibodies, including antigen-binding fragments thereof, such as heavy and light chain variable regions, comprise an amino acid sequence of the residues derived from Antibody A (light chain sequence=SEQ ID NO:18; heavy chain sequence=SEQ ID NO:19), Antibody B (light chain sequence=SEQ ID NO:18; heavy chain sequence=SEQ ID NO:20), Antibody C (light chain sequence=SEQ ID NO:21; heavy chain sequence=SEQ ID NO:19) or Antibody D (light chain sequence=SEQ ID NO:21; heavy chain sequence=SEQ ID NO:20).

In a further embodiment, the present invention provides an anti-IL-23p19 antibody or an antigen-binding fragment thereof that binds to human IL-23p19 at an epitope consisting of amino acid residues 108 to 126 and amino acid residues 137 to 151 of SEQ ID NO: 22.

In a further embodiment, the present invention provides an anti-IL-23p19 antibody or antigen-binding fragment thereof that competitively binds to human IL-23p19 with an antibody of the present invention, for example Antibody A, Antibody B, Antibody C or Antibody D described herein. The ability of an antibody or antigen-binding fragment to competitively bind to IL-23p19 can be measured using competitive binding assays known in the art.

In some embodiments, the present invention describes other humanized antibodies with light chain variable region sequences having the amino acid sequence set forth in of SEQ ID NO:10, 11, 12 or 13. In some embodiments, the present invention describes other humanized antibodies with heavy chain variable region sequences having the amino acid sequence set forth in of SEQ ID NO:14, 15, 16 or 17 (see Tables 3 and 4 above). The CDR sequences of these antibodies are shown in Tables 1 and 2. In particular, the present invention provides monoclonal antibodies with the combinations of light chain variable and heavy chain variable regions of SEQ ID NO: 11/14, 11/15, 10/14 or 10/15. Such variable regions can be combined with human constant regions.

In certain embodiments, the humanized anti-IL-23p19 antibody is an antibody fragment. Various antibody fragments have been generally discussed above and there are techniques that have been developed for the production of antibody fragments. Fragments can be derived via proteolytic digestion of intact antibodies (see, e.g., Morimoto et al., 1992, Journal of Biochemical and Biophysical Methods 24:107-117; and Brennan et al., 1985, Science 229:81). Alternatively, the fragments can be produced directly in recombinant host cells. For example, Fab'-SH fragments can be directly recovered from E. coli and chemically coupled to form F(ab')$_2$ fragments (see, e.g., Carter et al., 1992, Bio/Technology 10:163-167). By another approach, F(ab')$_2$ fragments can be isolated directly from recombinant host cell culture. Other techniques for the production of antibody fragments will be apparent to the skilled practitioner. Accordingly, in one aspect, the present invention provides antibody fragments comprising the CDRs described herein, in particular one of the combinations of L-CDR1, L-CDR2, L-CDR3, H-CDR1, H-CDR2 and H-CDR3 described herein. In a further aspect, the present invention provides antibody fragments comprising the variable regions described herein, for example one of the combinations of light chain variable regions and heavy chain variable regions described herein.

Certain embodiments include an F(ab')$_2$ fragment of a humanized anti-IL-23p19 antibody comprise a light chain sequence of any of SEQ ID NO: 18 or 21 in combination with a heavy chain sequence of SEQ ID NO: 19 or 20. Such embodiments can include an intact antibody comprising such an F(ab')$_2$.

In some embodiments, the antibody or antibody fragment includes a constant region that mediates effector function. The constant region can provide antibody-dependent cellular cytotoxicity (ADCC), antibody-dependent cellular phagocytosis (ADCP) and/or complement-dependent cytotoxicity (CDC) responses against an IL-23 expressing target cell. The effector domain(s) can be, for example, an Fc region of an Ig molecule.

The effector domain of an antibody can be from any suitable vertebrate animal species and isotypes. The isotypes from different animal species differ in the abilities to mediate effector functions. For example, the ability of human immunoglobulin to mediate CDC and ADCC/ADCP is generally in the order of IgM≈IgG$_1$≈IgG$_3$>IgG$_2$>IgG$_4$ and IgG$_1$≈IgG$_3$>IgG$_2$/IgM/IgG$_4$, respectively. Murine immunoglobulins mediate CDC and ADCC/ADCP generally in the order of murine IgM≈IgG$_3$>>IgG$_{2b}$>IgG$_{2a}$>>IgG$_1$ and IgG$_{2b}$>IgG$_{2a}$>IgG$_1$>>IgG$_3$, respectively. In another example, murine IgG$_{2a}$ mediates ADCC while both murine IgG$_{2a}$ and IgM mediate CDC.

Polynucleotides, Vectors, Host Cells, and Recombinant Methods

Other embodiments encompass isolated polynucleotides that comprise a sequence encoding a humanized anti-IL-23p19 antibody, vectors, and host cells comprising the polynucleotides, and recombinant techniques for production of the humanized antibody. The isolated polynucleotides can encode any desired form of the anti-IL-23p19 antibody including, for example, full length monoclonal antibodies, Fab, Fab', F(ab')$_2$, and Fv fragments, diabodies, linear antibodies, single-chain antibody molecules, and multispecific antibodies formed from antibody fragments.

The polynucleotide(s) that comprise a sequence encoding a humanized anti-IL-23p19 antibody or a fragment or chain thereof can be fused to one or more regulatory or control sequence, as known in the art, and can be contained in suitable expression vectors or host cell as known in the art. Each of the polynucleotide molecules encoding the heavy or light chain variable domains can be independently fused to a polynucleotide sequence encoding a constant domain, such as a human constant domain, enabling the production of intact antibodies. Alternatively, polynucleotides, or portions thereof, can be fused together, providing a template for production of a single chain antibody.

For recombinant production, a polynucleotide encoding the antibody is inserted into a replicable vector for cloning (amplification of the DNA) or for expression. Many suitable vectors for expressing the recombinant antibody are available. The vector components generally include, but are not limited to, one or more of the following: a signal sequence, an origin of replication, one or more marker genes, an enhancer element, a promoter, and a transcription termination sequence.

The humanized anti-IL-23p19 antibodies can also be produced as fusion polypeptides, in which the antibody is fused with a heterologous polypeptide, such as a signal sequence or other polypeptide having a specific cleavage site at the amino terminus of the mature protein or polypeptide.

The heterologous signal sequence selected is typically one that is recognized and processed (i.e., cleaved by a signal peptidase) by the host cell. For prokaryotic host cells that do not recognize and process the humanized anti-IL-23p19 antibody signal sequence, the signal sequence can be substituted by a prokaryotic signal sequence. The signal sequence can be, for example, alkaline phosphatase, penicillinase, lipoprotein, heat-stable enterotoxin II leaders, and the like. For yeast secretion, the native signal sequence can be substituted, for example, with a leader sequence obtained from yeast invertase alpha-factor (including *Saccharomyces* and *Kluyveromyces* α-factor leaders), acid phosphatase, *C. albicans* glucoamylase, or the signal described in WO90/13646. In mammalian cells, mammalian signal sequences as well as viral secretory leaders, for example, the herpes simplex gD signal, can be used. The DNA for such precursor region is ligated in reading frame to DNA encoding the humanized anti-IL-23p19 antibody.

Expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2-ν. plasmid origin is suitable for yeast, and various viral origins (SV40, polyoma, adenovirus, VSV, and BPV) are useful for cloning vectors in mammalian cells. Generally, the origin of replication component is not needed for mammalian expression vectors (the SV40 origin may typically be used only because it contains the early promoter).

Expression and cloning vectors may contain a gene that encodes a selectable marker to facilitate identification of expression. Typical selectable marker genes encode proteins that confer resistance to antibiotics or other toxins, e.g., ampicillin, neomycin, methotrexate, or tetracycline, or alternatively, are complement auxotrophic deficiencies, or in other alternatives supply specific nutrients that are not present in complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid, and hygromycin. Common selectable markers for mammalian cells are those that enable the identification of cells competent to take up a nucleic acid encoding a humanized anti-IL-23p19 antibody, such as DHFR (dihydrofolate reductase), thymidine kinase, metallothionein-I and -II (such as primate metallothionein genes), adenosine deaminase, ornithine decarboxylase, and the like. Cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., DG44).

Alternatively, host cells (particularly wild-type hosts that contain endogenous DHFR) transformed or co-transformed with DNA sequences encoding anti-IL-23p19 antibody, wild-type DHFR protein, and another selectable marker such as aminoglycoside 3'-phosphotransferase (APH), can be selected by cell growth in medium containing a selection agent for the selectable marker such as an aminoglycosidic antibiotic, e.g., kanamycin, neomycin, or G418. See, e.g., U.S. Pat. No. 4,965,199.

Where the recombinant production is performed in a yeast cell as a host cell, the TRP1 gene present in the yeast plasmid YRp7 (Stinchcomb et al., 1979, Nature 282: 39) can be used as a selectable marker. The TRP1 gene provides a selection marker for a mutant strain of yeast lacking the ability to grow in tryptophan, for example, ATCC No. 44076 or PEP4-1 (Jones, 1977, Genetics 85:12). The presence of the trpl lesion in the yeast host cell genome then provides an effective environment for detecting transformation by growth in the absence of tryptophan. Similarly, Leu2p-deficient yeast strains such as ATCC 20,622 and 38,626 are complemented by known plasmids bearing the LEU2 gene.

In addition, vectors derived from the 1.6 µm circular plasmid pKD1 can be used for transformation of *Kluyveromyces* yeasts. Alternatively, an expression system for large-scale production of recombinant calf chymosin was reported for *K. lactis* (Van den Berg, 1990, Bio/Technology 8:135). Stable multi-copy expression vectors for secretion of mature recombinant human serum albumin by industrial strains of *Kluyveromyces* have also been disclosed (Fleer et al., 1991, Bio/Technology 9:968-975).

Expression and cloning vectors usually contain a promoter that is recognized by the host organism and is operably linked to the nucleic acid molecule encoding an anti-IL-23p19 antibody or polypeptide chain thereof. Promoters suitable for use with prokaryotic hosts include phoA promoter, β-lactamase and lactose promoter systems, alkaline phosphatase, tryptophan (trp) promoter system, and hybrid promoters such as the tac promoter. Other known bacterial promoters are also suitable. Promoters for use in bacterial systems also will contain a Shine-Dalgarno (S.D.) sequence operably linked to the DNA encoding the humanized anti-IL-23p19 antibody.

Many eukaryotic promoter sequences are known. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Inducible promoters have the additional advantage of transcription controlled by growth conditions. These include yeast promoter regions for alcohol dehydrogenase 2, isocytochrome C, acid phosphatase, derivative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Humanized anti-IL-23p19 antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, or from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., 1982, Nature 297:598-601, disclosing expression of human p-interferon cDNA in mouse cells under the control of a thymidine kinase promoter from herpes simplex virus. Alternatively, the Rous sarcoma virus long terminal repeat can be used as the promoter.

Another useful element that can be used in a recombinant expression vector is an enhancer sequence, which is used to increase the transcription of a DNA encoding a humanized anti-IL-23p19 antibody by higher eukaryotes. Many enhancer sequences are now known from mammalian genes (e.g., globin, elastase, albumin, α-fetoprotein, and insulin). Typically, however, an enhancer from a eukaryotic cell virus is used. Examples include the SV40 enhancer on the late side of the replication origin (bp 100-270), the cytomegalovirus early promoter enhancer, the polyoma enhancer on the late side of the replication origin, and adenovirus enhancers. See also Yaniv, 1982, Nature 297:17-18 for a description of enhancing elements for activation of eukaryotic promoters. The enhancer may be spliced into the vector at a position 5' or 3' to the humanized anti-IL-23p19 antibody-encoding sequence, but is preferably located at a site 5' from the promoter.

Expression vectors used in eukaryotic host cells (yeast, fungi, insect, plant, animal, human, or nucleated cells from other multicellular organisms) can also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-IL-23p19 antibody. One useful transcription termination component is the bovine growth hormone polyadenylation region. See WO94/11026 and the expression vector disclosed therein. In some embodiments, humanized anti-IL-23p19 antibodies can be expressed using the CHEF system. (See, e.g., U.S. Pat. No. 5,888,809; the disclosure of which is incorporated by reference herein.)

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B,

*E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for humanized anti-IL-23p19antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402, 226); *Pichia* pastors (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger.*

Suitable host cells for the expression of glycosylated humanized anti-IL-23p19 antibody are derived from multi-cellular organisms. Examples of invertebrate cells include plant and insect cells, including, e.g., numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* (silk worm). A variety of viral strains for transfection are publicly available, e.g., the L-1 variant of *Autographa californica* NPV and the Bm-5 strain of *Bombyx mori* NPV, and such viruses may be used, particularly for transfection of *Spodoptera frugiperda* cells.

Plant cell cultures of cotton, corn, potato, soybean, petunia, tomato, and tobacco can also be utilized as hosts.

In another aspect, expression of humanized anti-IL-23p19 is carried out in vertebrate cells. The propagation of vertebrate cells in culture (tissue culture) has become routine procedure and techniques are widely available. Examples of useful mammalian host cell lines are monkey kidney CV1 line transformed by SV40 (COS-7, ATCC CRL 1651), human embryonic kidney line (293 or 293 cells subcloned for growth in suspension culture, (Graham et al., 1977, J. Gen Virol. 36: 59), baby hamster kidney cells (BHK, ATCC CCL 10), Chinese hamster ovary cells/-DHFR1 (CHO, Urlaub et al., 1980, Proc. Natl. Acad. Sci. USA 77: 4216; e.g., DG44), mouse sertoli cells (TM4, Mather, 1980, Biol. Reprod. 23:243-251), monkey kidney cells (CV1 ATCC CCL 70), African green monkey kidney cells (VERO-76, ATCC CRL-1587), human cervical carcinoma cells (HELA, ATCC CCL 2), canine kidney cells (MDCK, ATCC CCL 34), buffalo rat liver cells (BRL 3A, ATCC CRL 1442), human lung cells (W138, ATCC CCL 75), human liver cells (Hep G2, HB 8065), mouse mammary tumor (MMT 060562, ATCC CCL51), TR1 cells (Mather et al., 1982, Annals N.Y. Acad. Sci. 383: 44-68), MRC 5 cells, FS4 cells, and human hepatoma line (Hep G2).

Host cells are transformed with the above-described expression or cloning vectors for humanized anti-IL-23p19 antibody production and cultured in conventional nutrient media modified as appropriate for inducing promoters, selecting transformants, or amplifying the genes encoding the desired sequences.

The host cells used to produce a humanized anti-IL-23p19 antibody described herein may be cultured in a variety of media. Commercially available media such as Ham's F10 (Sigma-Aldrich Co., St. Louis, Mo.), Minimal Essential Medium ((MEM), (Sigma-Aldrich Co.), RPMI-1640 (Sigma-Aldrich Co.), and Dulbecco's Modified Eagle's Medium ((DMEM), Sigma-Aldrich Co.) are suitable for culturing the host cells. In addition, any of the media described in one or more of Ham et al., 1979, Meth. Enz. 58: 44, Barnes et al., 1980, Anal. Biochem. 102: 255, U.S. Pat. Nos. 4,767,704, 4,657,866, 4,927,762, 4,560,655, 5,122,469, WO 90/103430, and WO 87/00195 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamicin), trace elements (defined as inorganic compounds usually present at final concentrations in the micromolar range), and glucose or an equivalent energy source. Other supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, the cells may be disrupted to release protein as a first step. Particulate debris, either host cells or lysed fragments, can be removed, for example, by centrifugation or ultrafiltration. Carter et al., 1992, Bio/Technology 10:163-167 describes a procedure for isolating antibodies that are secreted to the periplasmic space of *E. coli*. Briefly, cell paste is thawed in the presence of sodium acetate (pH 3.5), EDTA, and phenylmethylsulfonylfluoride (PMSF) over about 30 minutes. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants. A variety of methods can be used to isolate the antibody from the host cell.

The antibody composition prepared from the cells can be purified using, for example, hydroxylapatite chromatography, gel electrophoresis, dialysis, and affinity chromatography, with affinity chromatography being a typical purification technique. The suitability of protein A as an affinity ligand depends on the species and isotype of any immunoglobulin Fc domain that is present in the antibody. Protein A can be used to purify antibodies that are based on human gamma1, gamma2, or gamma4 heavy chains (see, e.g., Lindmark et al., 1983 J. Immunol. Meth. 62:1-13). Protein G is recommended for all mouse isotypes and for human gamma3 (see, e.g., Guss et al., 1986 EMBO J. 5:1567-1575). A matrix to which an affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the Bakerbond ABX™ resin (J. T. Baker, Phillipsburg, N.J.) is useful for purification. Other techniques for protein purification such as fractionation on an ion-exchange column, ethanol precipitation, reverse phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, typically performed at low salt concentrations (e.g., from about 0-0.25M salt).

Kits Using Biomarkers

One or more biomarkers disclosed herein (for example β-defensin 2, neutrophil gelatinase lipocalin, and S-100 proteins) can be developed into an analytical method, for example an assay kit, a test stick or another diagnostic device, for example for predicting response to an anti-IL-23p19 antibody either prior to treatment or early after initiation of treatment of patients. In one aspect, such analytical method includes a packaged combination of reagents in predetermined amounts, with or without a analytical device, with instructions for performing the diagnostic assay. Where specific antibodies are labeled with an enzyme or a dye or a radioactive isotope, the kit may include substrates and cofactors required by the enzyme such as a substrate precursor that provides the detectable chromophore or fluorophore. In addition, other additives may be included such as stabilizers, buffers (for example a block buffer or lysis buffer), and the like. The relative amounts of the various reagents may be varied widely to provide for concentrations in solution of the reagents that substantially optimize the sensitivity of the assay. The reagents may be provided as dry powders, usually lyophilized, including excipients that on dissolution will provide a reagent solution having the appropriate concentration or as solutions.

Therapeutic Uses

In another embodiment, a humanized anti-IL-23p19 antibody disclosed herein is useful in the treatment of various disorders associated with the expression of IL-23p19 as described herein. Methods for treating an IL-23 associated disorder comprise administering a therapeutically effective amount of a humanized anti-IL-23p19 antibody to a subject in need thereof.

The humanized anti-IL-23p19 antibody or agent is administered by any suitable means, including parenteral, subcutaneous, intraperitoneal, intrapulmonary, and intranasal, and, if desired for local immunosuppressive treatment, intralesional administration (including perfusing or otherwise contacting the graft with the antibody before transplantation). The humanized anti-IL-23p19 antibody or agent can be administered, for example, as an infusion or as a bolus. Parenteral infusions include intramuscular, intravenous, intraarterial, intraperitoneal, or subcutaneous administration. In addition, the humanized anti-IL-23p19 antibody is suitably administered by pulse infusion, particularly with declining doses of the antibody. In one aspect, the dosing is given by injections, most preferably intravenous or subcutaneous injections, depending in part on whether the administration is brief or chronic.

For the prevention or treatment of disease, the appropriate dosage of antibody will depend on a variety of factors such as the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 μg/kg to 20 mg/kg (e.g., 0.1-15 mg/kg) of antibody is an initial candidate dosage for administration to the patient, whether, for example, by one or more separate administrations, or by continuous infusion. A typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is that disclosed in WO 94/04188.

The term "suppression" is used herein in the same context as "amelioration" and "alleviation" to mean a lessening of one or more characteristics of the disease.

The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary to prevent, ameliorate, or treat the disorder associated with IL-23 expression.

The antibody need not be, but is optionally, formulated with one or more agents currently used to prevent or treat the disorder in question. The effective amount of such other agents depends on the amount of humanized anti-IL-23p19 antibody present in the formulation, the type of disorder or treatment, and other factors discussed above. These are generally used in the same dosages and with administration routes as used hereinbefore or about from 1 to 99% of the heretofore employed dosages.

IL-23-Associated Disorders

The anti-IL-23p19 antibodies or agents are useful for treating or preventing an immunological disorder characterized by abnormal expression of IL-23, e.g., by inappropriate activation of immune cells (e.g., lymphocytes or dendritic cells). Such abnormal expression of IL-23 can be due to, for example, increased IL-23 protein levels.

Immunological diseases that are characterized by inappropriate activation of immune cells and that can be treated or prevented by the methods described herein can be classified, for example, by the type(s) of hypersensitivity reaction(s) that underlie the disorder. These reactions are typically classified into four types: anaphylactic reactions, cytotoxic (cytolytic) reactions, immune complex reactions, or cell-mediated immunity (CMI) reactions (also referred to as delayed-type hypersensitivity (DTH) reactions). (See, e.g., Fundamental Immunology (William E. Paul ed., Raven Press, N.Y., 3rd ed. 1993).) Immunological diseases include inflammatory diseases and autoimmune diseases.

Specific examples of immunological diseases include the following: psoriasis, inflammatory bowel disease, for example ulcerative colitis or Crohn's disease, and spondyloarthritis, for example ankylosing spondylitis, non-radiographic axial spondyloarthritis, peripheral spondyloarthritis or psoriatic arthritis.

In one aspect, the immunological disease is psoriasis. Psoriasis is a chronic inflammatory disease of the skin characterized by dysfunctional keratinocyte differentiation and hyperproliferation and marked accumulation of inflammatory T cells and dendritic cells. For example, the immunological disease includes plaque psoriasis, for example chronic plaque psoriasis, for example moderate to severe chronic plaque psoriasis, for example in patients who are candidates for systemic therapy or phototherapy. For example, the immunological disease includes palmar pustular psoriasis, guttate psoriasis, inverse psoriasis, pustular psoriasis or erythrodermic psoriasis.

Pharmaceutical Compositions and Administration Thereof

A composition comprising an IL-23p19 binding agent (e.g., an anti-IL-23p19 antibody) can be administered to a subject having or at risk of having an immunological disorder. The invention further provides for the use of a IL-23p19 binding agent (e.g., an anti-IL-23p19 antibody) in the manufacture of a medicament for prevention or treatment of an immunological disorder. The term "subject" as used herein means any mammalian patient to which an IL-23p19 binding agent can be administered, including, e.g., humans and non-human mammals, such as primates, rodents, and dogs. Subjects specifically intended for treatment using the methods described herein include humans. The antibodies or agents can be administered either alone or in combination with other compositions in the prevention or treatment of the immunological disorder.

Further examples of antibodies for use in such pharmaceutical compositions are also those that comprise a humanized antibody or antibody fragment having the light chain variable region amino acid sequence of any of SEQ ID NO:10, 11, 12 or 13. Preferred antibodies for use in such pharmaceutical compositions are also those that comprise a humanized antibody or antibody fragment having the heavy chain variable region amino acid sequence of any of SEQ ID NO:14, 15, 16 or 17.

Further examples of antibodies for use in such pharmaceutical compositions are also those that comprise a humanized antibody or antibody fragment having the light chain variable region and heavy chain variable region of any of SEQ ID NO: 11 and 14, SEQ ID NO: 11 and 15, SEQ ID NO: 10 and 14 or SEQ ID NO: 10 and 15.

Further examples of antibodies for use in such pharmaceutical compositions are also those that comprise a humanized antibody having the light chain region amino acid sequence of any of SEQ ID NO:18 or 21. Preferred antibodies for use in such pharmaceutical compositions are also those that comprise humanized antibody having the heavy chain variable region amino acid sequence of any of SEQ ID NO:19 or 20.

Further examples of antibodies for use in such pharmaceutical compositions are also those that comprise Antibody A, Antibody B, Antibody C or Antibody D.

Various delivery systems are known and can be used to administer the IL-23p19 binding agent. Methods of introduction include but are not limited to intradermal, intramuscular, intraperitoneal, intravenous, subcutaneous, intranasal, epidural, and oral routes. The IL-23p19 binding agent can be administered, for example by infusion, bolus or injection, and can be administered together with other biologically active agents such as chemotherapeutic agents. Administration can be systemic or local. In preferred embodiments, the administration is by subcutaneous injection. Formulations for such injections may be prepared in for example prefilled syringes that may be administered once every other week.

In specific embodiments, the IL-23p19 binding agent composition is administered by injection, by means of a catheter, by means of a suppository, or by means of an implant, the implant being of a porous, non-porous, or gelatinous material, including a membrane, such as a sialastic membrane, or a fiber. Typically, when administering the composition, materials to which the anti-IL-23p19 antibody or agent does not absorb are used.

In other embodiments, the anti-IL-23p19 antibody or agent is delivered in a controlled release system. In one embodiment, a pump may be used (see, e.g., Langer, 1990, Science 249:1527-1533; Sefton, 1989, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used. (See, e.g., Medical Applications of Controlled Release (Langer and Wise eds., CRC Press, Boca Raton, Fla., 1974); Controlled Drug Bioavailability, Drug Product Design and Performance (Smolen and Ball eds., Wiley, New York, 1984); Ranger and Peppas, 1983, Macromol. Sci. Rev. Macromol. Chem. 23:61. See also Levy et al., 1985, Science 228:190; During et al., 1989, Ann. Neurol. 25:351; Howard et al., 1989, J. Neurosurg. 71:105.) Other controlled release systems are discussed, for example, in Langer, supra.

An IL-23p19 binding agent (e.g., an anti-IL-23p19 antibody) can be administered as pharmaceutical compositions comprising a therapeutically effective amount of the binding agent and one or more pharmaceutically compatible ingredients.

In typical embodiments, the pharmaceutical composition is formulated in accordance with routine procedures as a pharmaceutical composition adapted for intravenous or subcutaneous administration to human beings. Typically, compositions for administration by injection are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration.

Further, the pharmaceutical composition can be provided as a pharmaceutical kit comprising (a) a container containing a IL-23p19 binding agent (e.g., an anti-IL-23p19 antibody) in lyophilized form and (b) a second container containing a pharmaceutically acceptable diluent (e.g., sterile water) for injection. The pharmaceutically acceptable diluent can be used for reconstitution or dilution of the lyophilized anti-IL-23p19 antibody or agent. Optionally associated with such container(s) can be a notice in the form prescribed by a governmental agency regulating the manufacture, use or sale of pharmaceuticals or biological products, which notice reflects approval by the agency of manufacture, use or sale for human administration.

Examples of pharmaceutical compositions used in the context of the present invention are disclosed in Example 2 hereinbelow.

The amount of the IL-23p19 binding agent (e.g., anti-IL-23p19 antibody) that is effective in the treatment or prevention of an immunological disorder can be determined by standard clinical techniques. In addition, in vitro assays may optionally be employed to help identify optimal dosage ranges. The precise dose to be employed in the formulation will also depend on the route of administration, and the stage of immunological disorder, and should be decided according to the judgment of the practitioner and each patient's circumstances. Effective doses may be extrapolated from dose-response curves derived from in vitro or animal model test systems.

Generally, the dosage of an anti-IL-23p19 antibody or IL-23p19 binding agent administered to a patient with an immunological disorder is typically about 0.1 mg/kg to about 100 mg/kg of the subject's body weight. The dosage administered to a subject is about 0.1 mg/kg to about 50 mg/kg, about 1 mg/kg to about 30 mg/kg, about 1 mg/kg to about 20 mg/kg, about 1 mg/kg to about 15 mg/kg, or about 1 mg/kg to about 10 mg/kg of the subject's body weight.

Exemplary doses include, but are not limited to, from 1 ng/kg to 100 mg/kg. In some embodiments, a dose is about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg or about 16 mg/kg. The dose can be administered, for example, daily, once per week (weekly), twice per week, thrice per week, four times per week, five times per week, six times per week, biweekly or monthly, every two months, or every three months. In specific embodiments, the dose is about 0.5 mg/kg/week, about 1 mg/kg/week, about 2 mg/kg/week, about 3 mg/kg/week, about 4 mg/kg/week, about 5 mg/kg/week, about 6 mg/kg/week, about 7 mg/kg/week, about 8 mg/kg/week, about 9 mg/kg/week, about 10 mg/kg/week, about 11 mg/kg/week, about 12 mg/kg/week, about 13 mg/kg/week, about 14 mg/kg/week, about 15 mg/kg/week or about 16 mg/kg/week. In some embodiments, the dose ranges from about 1 mg/kg/week to about 15 mg/kg/week.

In some embodiments, the pharmaceutical compositions comprising the IL-23p19 binding agent can further comprise a therapeutic agent, either conjugated or unconjugated to the binding agent. The anti-IL-23p19 antibody or IL-23p19 binding agent can be co-administered in combination with one or more therapeutic agents for the treatment or prevention of immunological disorders.

Such combination therapy administration can have an additive or synergistic effect on disease parameters (e.g., severity of a symptom, the number of symptoms, or frequency of relapse).

With respect to therapeutic regimens for combinatorial administration, in a specific embodiment, an anti-IL-23p19 antibody or IL-23p19 binding agent is administered concurrently with a therapeutic agent. In another specific embodiment, the therapeutic agent is administered prior or subsequent to administration of the anti-IL-23p19 antibody or IL-23p19 binding agent, by at least an hour and up to several months, for example at least an hour, five hours, 12 hours, a day, a week, a month, or three months, prior or subsequent to administration of the anti-IL-23p19 antibody or IL-23p19 binding agent.

The invention is further described in the following examples, which are not intended to limit the scope of the invention.

EXAMPLES

Example 1: Study

Study Design

This is a multi-centre, randomised, parallel assignment, double-blind, single-rising-dose, placebo-controlled, within-dose cohort trial. Following a 6-week screening period, patients were assigned to one of the two experimental arms. In the first arm, patients were randomised and allocated to one of six sequential dose cohorts (0·01, 0·05, 0·25, 1, 3, and 5 mg/kg) and randomised to receive a single dose of Antibody A or placebo intravenously (IV); four patients were included in each cohort (3:1 ratio; Antibody A:placebo). In the second arm, patients were randomised and allocated to one of two parallel dose groups (0·25 and 1 mg/kg) and randomised to receive Antibody A or placebo subcutaneously (SC); seven patients were planned for each cohort (6:1 ratio; Antibody A to placebo). Sample size was based on commonly used values for single-rising-dose studies and was not calculated according to hypotheses testing.

Antibody A IV dose groups were enrolled sequentially and Antibody A SC dose groups were randomised in parallel. Active versus placebo allocation within each cohort was double-blinded, but, for both IV and SC arms, cohorts were not blinded and were known to investigators and patients.

Central randomisation and blinded assignment of medication was performed via an interactive response tool. The randomisation list was generated using a validated system incorporating a pseudo-random number generator and supplied seed number. Access to randomisation codes was controlled and documented.

All patients were followed up for 24 weeks. A protocol amendment permitted patients receiving Antibody A SC who had at least a 50% improvement in psoriasis area severity index (≥PASI 50) from baseline to Week 24 to be offered enrolment into an optional observational follow-up period.

Patients

Eligible patients were aged 18-75 years, with chronic moderate-to-severe plaque psoriasis, lasting ≥6 months, with BSA involvement of ≥10, PASI≥12, and Static Physicians Global Assessment (sPGA) score of moderate and above. Female patients were not of childbearing potential and patients had a Body Mass Index of ≥18.5 but <40.

Key exclusion criteria included patients who had received prior treatment with: ustekinumab within 24 weeks, other biologic agents or psoralen and ultraviolet A (PUVA) within 12 weeks, UVB phototherapy and oral anti-psoriatic medications within 4 weeks, or topical-anti-psoriasis medications (except emollients) within 2 weeks prior to study dosing. Patients with current or previous clinically significant psoriatic disease, medical condition other than psoriasis or medical examination finding were also excluded from this study on the basis of the investigator's clinical judgement. Patients with chronic or relevant acute infections including hepatitis and tuberculosis (or a positive interferon-γ release assay at screening) were also excluded from the study.

Study Medication and Dosage

For IV administration, Antibody A (10 mg/mL) or placebo solution was injected into a 100 mL IV infusion bag of normal saline solution. Antibody A (90 mg/mL) or placebo pre-filled syringes were administered SC without dilution; excess volume was discarded.

Endpoints

The primary endpoint was safety and tolerability of Antibody A and was assessed descriptively based on physical examination, vital signs, electrocardiogram (ECG), clinical laboratory tests, adverse event (AE) reporting, and assessment of local and global tolerability by the investigator. Secondary clinical endpoints included PASI percentage change from baseline and sPGA at Weeks 4, 8, 12, and 24. Patient photographs were obtained as part of the study protocol. Secondary pharmacokinetic endpoints were also evaluated, along with pharmacodynamic endpoints.

Histopathology, Immunohistochemistry, and RNA-Sequencing

Skin 6 mm punch biopsy samples were obtained from all patients at Baseline from a representative psoriatic lesion and at Week 8 from the same area. Biopsies were processed for histopathology, immunohistochemistry, and RNA-sequencing analysis.

Tissue sections were stained. Histopathology was based on haematoxylin and eosin staining. Sections were also stained with specific antibodies and evaluated semi-quantitatively for the presence of keratinocyte-related markers (K16 and Ki67), markers associated with tissue inflammation (5-100A7, neutrophil gelatinase lipocalin, β-defensin 2), dendritic cell lysosome associated membrane glycoprotein (DC-LAMP), CD11c (dermal dendritic cell marker), and CD3 (activate T-cell marker). In addition, RNA was extracted from skin biopsy samples for subsequent global transcriptome-wide RNA sequencing using the Illumina Hi-Seq 2000 (Illumina Inc., San Diego, Calif.).

Statistical Analysis

Comparisons of safety, clinical efficacy and biomarkers of Antibody A were summarised between Antibody A dose groups and placebo descriptively. In patients receiving rescue treatments after experiencing an intolerable increase in disease activity, efficacy endpoints assessed after administration of restricted medications were censored or last pre-rescue observation was carried forward (continuous).

A generalised linear model on the RNA-sequence count data was fit using empirical Bayes estimates of the dispersion (variance). The model included different covariates, yielding estimates of the adjusted fold change and p-value for each transcript. The false discovery rate was computed for each transcript and a p-value threshold determined. Gene expression fold changes for each patient dataset were calculated according to the following equation: (Antibody A—treatment value at Week 8/value at Baseline)/(Placebo-treatment value at Week 8/value at Baseline).

The Gene Ontology (GO) pathway sub-analysis used an approach, which estimates the enrichment ratio and p-value for gene sets relative to the background (all human genes, Huang et al, Genome Biol. 2007; 8:R183. Published microarray data were downloaded from the Gene Expression Omnibus database (ncbi.nlm.nih.gov/geo) and a robust multi-array average normalisation used. Empirical Bayes t-tests/ANOVA models computed fold changes and p-values were calculated for each gene.

Results

Of 73 patients screened, 39 were eligible; 24 were randomised to six Antibody A IV cohorts and 14 to two Antibody A SC cohorts. One patient originally randomised to receive 1 mg/kg SC inadvertently received the 0.25 mg/kg dose. An additional patient was, therefore, assigned to the 1 mg/kg cohort, so that seven and six patients were included in the 0.25 and 1 mg/kg SC cohort, respectively. All 39 patients received a single dose of Antibody A or placebo and completed the 24-week follow-up except one patient in the 5 mg/kg IV group who discontinued follow-up after Week 12 due to relocation.

Baseline demographics were similar across all treatment groups; patients had similar duration of disease and were comparable within the SC and IV cohorts. Mean PASI scores ranged from 157 to 22.8, with individual subject scores at randomisation ranging from 10.5 to 43.4.

Overall, in patients receiving IV or SC Antibody A, a 75, 90, and 100% decrease in PASI was achieved by 87% ($^{27}/_{31}$), 58% ($^{18}/_{31}$), and 16% ($^{5}/_{31}$) of patients at Week 12, respectively; no patients receiving placebo achieved these improvements in PASI score (Table 6). At Week 24, PASI 75 was achieved by 68% of Antibody A patients, overall ($^{22}/_{31}$); only one placebo patient (13%) achieved PASI 75 at Week 24. PASI 90 and 100 rates at Week 24 were achieved by 48% ($^{15}/_{31}$) and 29% ($^{9}/_{31}$) of Antibody A patients, respectively; no patients in the placebo cohort achieved these PASI improvements. Within 24 weeks of the single Antibody A dose, 96%, 84%, and 64% of patients in Antibody A dose groups ≥0·25 mg/kg (n=25) achieved PASI 75, PASI 90, and PASI 100, respectively.

Assessments of sPGA were consistent with PASI; all SC Antibody A patients achieving "clear" or "almost clear" at both Weeks 12 and 24 (Table 6) and clinical improvements were confirmed by lesion photographs.

Improvements in PASI scores in Antibody A cohorts were observed as early as Week 2. Further PASI score improvements were observed through to Week 8 and were maintained until Week 24 (FIG. 1). All SC Antibody A patients had PASI 75 at Week 24. A protocol amendment extended their follow-up beyond Week 24 to evaluate the durability of this response to Antibody A. Eight of 13 patients who received SC Antibody A were eligible and chose to enroll into this optional observational follow-up. Six of eight patients maintained PASI 100 at a range of 41 to 66 weeks after a single dose (data not shown).

TABLE 6

PASI score improvements and sPGA classification rates at Weeks 12 and 24

| | | Method of administration of Antibody A | | | | | | | |
|---|---|---|---|---|---|---|---|---|---|
| | | IV | | | | | | SC | |
| Antibody A dose | | 0.01 mg/kg | 0.05 mg/kg | 0.25 mg/kg | 1 mg/kg | 3 mg/kg | 5 mg/kg | 0.25 mg/kg | 1 mg/kg |
| N | | 3 | 3 | 3 | 3 | 3 | 2 | 7 | 6 |
| PASI 75 | Week 12 | 3 | 1 | 3 | 2 | 3 | 3 | 6 | 6 |
| | Week 24 | 1 | 0 | 3 | 2 | 2 | 1$^a$ | 7 | 6 |
| PASI 90 | Week 12 | 3 | 0 | 2 | 2 | 2 | 2 | 4 | 3 |
| | Week 24 | 0 | 0 | 1 | 2 | 1 | 1$^a$ | 5 | 6 |
| PASI 100 | Week 12 | 0 | 0 | 0 | 1 | 0 | 1 | 2 | 1 |
| | Week 24 | 0 | 0 | 1 | 1 | 0 | 1$^a$ | 3 | 4 |

TABLE 6-continued

PASI score improvements and sPGA classification rates at Weeks 12 and 24

| sPGA "clear" or "almost clear" | Week 12 | 3 | 1 | 2 | 2 | 3 | 3 | 7 | 6 |
|---|---|---|---|---|---|---|---|---|---|
| | Week 24 | 1 | 0 | 1 | 2 | 2 | 1[a] | 7 | 6 |

| Antibody A dose | | Overall Antibody A | Placebo |
|---|---|---|---|
| N | | 31 | 8 |
| PASI 75 | Week 12 | 27 | 0 |
| | Week 24 | 22 | 1 |
| PASI 90 | Week 12 | 18 | 0 |
| | Week 24 | 15 | 0 |
| PASI 100 | Week 12 | 5 | 0 |
| | Week 24 | 9 | 0 |
| sPGA "clear" or "almost clear" | Week 12 | 27 | 0 |
| | Week 24 | 20 | 0 |

Number of patients in each treatment group achieving PASI 75-100 and a favourable sPGA at Week 12 and Week 24. N values represent the number of patients per group at Baseline; all patients were analysed at Week 12 and Week 24, except where indicated. Overall Antibody A values are given as totals for the Antibody A groups.

[a]N=2 due to relocation of a patient in the 5 mg/kg group.

IV, intravenous; PASI, Psoriasis Area Severity Index; SC, subcutaneous; sPGA, Static Physicians Global Assessment. Histopathology, Immunohistochemistry, and RNA-Sequencing Single doses of Antibody A resulted in marked reductions from Baseline to Week 8 in hyperkeratosis with parakeratosis, epidermal acanthosis, and generalised inflammation in the dermis and epidermis. Treatment with Antibody A resulted in decreases in markers associated with thickening of the keratinocyte layer (K16) and hyperproliferation (Ki67), dermal infiltration by T-cells (CD3), neutrophils (neutrophil gelatinase lipocalin), dendritic cells (CD11c and DC-LAMP), and tissue inflammation (β-defensin 2, 5-100A8/A9) at Week 8. These changes in the skin biopsy markers were primarily observed in patients from IV and SC Antibody A dose cohorts ≥0.25 mg/kg compared with placebo, across the different markers.

Treatment with Antibody A also resulted in significant (>2 fold) reductions ($p<0.005$) in the expression of 199 genes (IV) and 226 genes (SC) relative to placebo in patient skin biopsies (comparing Baseline to Week 8). The overlap between these two cohorts was 192 genes. This gene set included genes associated with the IL-23/IL-17 axis (IL-23A, IL-23R, IL-22, IL-22RA1 RA2, IL-17A, IL-17F, IL-17RA, and IL-17RC), keratinocyte and epithelial cell differentiation (late cornified envelope protein, transglutaminase 1, and cornifelin), tissue inflammation (β-defensin 2, neutrophil gelatinase lipocalin, and S-100A7/A8), and the IFNα pathway (IFIH1, ISG15, IRF7, IFI44, MX1, MX2, STAT1, and TRIM22). GO pathway analysis also showed significant modulation of the pathways represented by these genes (Table 7).

TABLE 7

Summary of GO: Pathway analysis of the 79 gene cluster post-treatment with Antibody A

| Term | Count | p p-value | Genes | Fold enrichment |
|---|---|---|---|---|
| GO: 0009615~response to virus | 9 | 2.48E−08 | IFIH1, ISG15, IRF7, RSAD2, IFI44, MX1, STAT1, MX2, TRIM22 | 18.31133 |
| GO: 0031424~keratinization | 4 | 9.02E−04 | LCE3D, TGM1, CNFN, LCE3E | 20.62981 |
| GO: 0030216~keratinocyte differentiation | 4 | 0.003113 | LCE3D, TGM1, CNFN, LCE3E | 13.44064 |
| GO: 0030855~epithelial cell differentiation | 5 | 0.003166 | LCE3D, TGM1, CNFN, DHRS9, LCE3E | 8.093814 |
| GO: 0009913~epidermal cell differentiation | 4 | 0.003981 | LCE3D, TGM1, CNFN, LCE3E | 12.32058 |
| GO: 0009310~amine catabolic process | 4 | 0.004984 | ARG1, KYNU, HAL, SMOX | 11.37285 |
| REACT_13: Metabolism of amino acids | 4 | 0.00735 | ARG1, KYNU, HAL, SMOX | 8.33865 |
| GO: 0009063~cellular amino acid catabolic process | 3 | 0.03655 | ARG1, KYNU, HAL | 9.783992 |
| hsa04622: RIG-I-like receptor signaling pathway | 3 | 0.043535 | IFIH1, ISG15, IRF7 | 8.594366 |

Enriched RNAs following treatment with Antibody A were identified relative to background using a previously described methodology {Huang et al. Genome Biol 2007}. GO pathways were identified using published microarray data (ncbi.nlm.nih.gov/geo) and a robust multi-array average normalisation. Empirical Bayes t-tests or ANOVA models computed fold changes and p-values were calculated for each gene {Huang et al. Genome Biol 2007}. HGNC gene names are used.

GO, Gene ontology; RNA, ribonucleic acid; HGNC, HUGO Gene Nomenclature Committee.

Of the Antibody A-responsive gene set, expression of a subset of 79 genes was decreased following treatment with Antibody A and significantly correlated with PASI scores at Week 8 ($r=0.73$, $p=2\times10^{-6}$). Reductions in IL-23A and IL-23R expression were also significantly correlated with PASI scores at Week 8 ($r=0.57$ and $r=0.54$; $p<0.005$). In addition, Antibody A treatment led to normalisation of a gene set previously reported to distinguish lesional and non-lesional tissue from psoriasis patients. Importantly, this gene set had significant overlap (91%) with the Antibody A-responsive gene set that correlated with PASI scores.

The results are summarized in Table 8, which indicates the 79 gene transcripts, full names and fold changes (p values). Gene expression fold changes for each patient dataset were calculated according to the following equation: (Antibody A-treatment value at Week 8/value at Baseline)/(Placebo-treatment value at Week 8/value at Baseline).

TABLE 8

| Transcript | Trt FC | p.value | Name |
|---|---|---|---|
| PRSS22 | 0.22 | 0.001309 | protease, serine, 22 |
| TYMP | 0.187 | 0.001765 | thymidine phosphorylase |
| MXD1 | 0.516 | 0.000498 | MAX dimerization protein 1 |
| DHRS9 | 0.333 | 0.003122 | dehydrogenase/reductase (SDR family) member 9 |
| ATP12A | 0.131 | 0.002618 | ATPase, H+/K+ transporting, nongastric, alpha polypeptide |
| HAL | 0.348 | 0.006686 | histidine ammonia-lyase |
| SMOX | 0.368 | 0.000122 | spermine oxidase |
| TGM1 | 0.29 | 5.52E-05 | transglutaminase 1 (K polypeptide epidermal type I, protein-glutamine-gamma-glutamyltransferase) |
| VNN3 | 0.229 | 0.000265 | vanin 3 |
| PLA2G3 | 0.474 | 0.002278 | phospholipase A2, group III |
| SLC5A1 | 0.4 | 0.001253 | solute carrier family 5 (sodium/glucose cotransporter), member 1 |
| APOL1 | 0.308 | 0.011199 | apolipoprotein L, 1 |
| GDPD3 | 0.429 | 0.000346 | glycerophosphodiester phosphodiesterase domain containing 3 |
| SMPD3 | 0.38 | 0.000115 | sphingomyelin phosphodiesterase 3, neutral membrane (neutral sphingomyelinase II) |
| SQLE | 0.503 | 0.000211 | squalene epoxidase |
| CNFN | 0.239 | 1.52E-05 | cornifelin |
| HYAL4 | 0.218 | 4.60E-07 | hyaluronoglucosaminidase 4 |
| OAS3 | 0.29 | 0.001929 | 2'-5'-oligoadenylate synthetase 3, 100 kDa |
| OAS2 | 0.192 | 0.003705 | 2'-5'-oligoadenylate synthetase 2, 69/71 kDa |
| HRH2 | 0.373 | 0.002386 | histamine receptor H2 |
| IFIH1 | 0.425 | 0.008001 | interferon induced with helicase C domain 1 |
| STAT1 | 0.459 | 0.012805 | signal transducer and activator of transcription 1, 91 kDa |
| KYNU | 0.249 | 0.001811 | kynureninase |
| FLVCR2 | 0.44 | 0.000454 | feline leukemia virus subgroup C cellular receptor family, member 2 |
| IFIT3 | 0.291 | 0.002822 | interferon-induced protein with tetratricopeptide repeats 3 |
| NT5C3 | 0.421 | 0.000717 | 5'-nucleotidase, cytosolic III |
| IFI6 | 0.103 | 0.000325 | interferon, alpha-inducible protein 6 |
| KLK10 | 0.336 | 0.000902 | kallikrein-related peptidase 10 |
| KLHDC7B | 0.304 | 0.000148 | kelch domain containing 7B |
| SCO2 | 0.339 | 0.004546 | SCO2 cytochrome c oxidase assembly protein |

TABLE 8-continued

| Transcript | Trt FC | p.value | Name |
|---|---|---|---|
| HELZ2 | 0.365 | 0.000531 | helicase with zinc finger 2, transcriptional coactivator |
| TRIM22 | 0.422 | 0.0375 | tripartite motif containing 22 |
| EPSTI1 | 0.26 | 0.003714 | epithelial stromal interaction 1 (breast) |
| RSAD2 | 0.225 | 0.001466 | radical S-adenosyl methionine domain containing 2 |
| CMPK2 | 0.255 | 0.001387 | cytidine monophosphate (UMP-CMP) kinase 2, mitochondrial |
| TCN1 | 0.083 | 0.000784 | transcobalamin I (vitamin B12 binding protein, R binder family) |
| OASL | 0.122 | 5.35E-05 | 2'-5'-oligoadenylate synthetase-like |
| DDX60 | 0.407 | 0.009311 | DEAD (Asp-Glu-Ala-Asp) box polypeptide 60 ('DEAD (Asp-Glu-Ala-Asp)' disclosed as SEQ ID NO: 23) |
| IFI44L | 0.211 | 0.005291 | interferon-induced protein 44-like |
| IFI44 | 0.283 | 0.012865 | interferon-induced protein 44 |
| PARP9 | 0.391 | 0.010339 | poly (ADP-ribose) polymerase family, member 9 |
| HERC6 | 0.189 | 0.001701 | HECT and RLD domain containing E3 ubiquitin protein ligase family member 6 |
| EPHA2 | 0.438 | 5.27E-06 | EPH receptor A2 |
| UBE2L6 | 0.418 | 0.002472 | ubiquitin-conjugating enzyme E2L6 |
| MX1 | 0.185 | 0.000774 | myxovirus (influenza virus) resistance 1, interferon-inducible protein p78 (mouse) |
| PLA2G2F | 0.349 | 0.000271 | phospholipase A2, group IIF |
| HK2 | 0.527 | 0.021317 | hexokinase 2 |
| GBAP1 | 0.366 | 0.000729 | glucosidase, beta, acid pseudogene 1 |
| PDZK1IP1 | 0.349 | 0.000932 | PDZK1 interacting protein 1 |
| LCE3D | 0.144 | 0.004114 | late cornified envelope 3D |
| ZC3H12A | 0.236 | 0.000427 | zinc finger CCCH-type containing 12A |
| IFI27 | 0.289 | 0.006965 | interferon, alpha-inducible protein 27 |
| ANGPTL4 | 0.318 | 0.003141 | angiopoietin-like 4 |
| FUT3 | 0.342 | 0.001375 | fucosyltransferase 3 (galactoside 3(4)-L-fucosyltransferase, Lewis blood group) |
| LRG1 | 0.237 | 0.001718 | leucine-rich alpha-2-glycoprotein 1 |
| PRSS27 | 0.192 | 0.00072 | protease, serine 27 |
| HPSE | 0.211 | 0.000233 | heparanase |
| FBXO45 | 0.507 | 0.002771 | F-box protein 45 |
| SLC26A9 | 0.282 | 0.000288 | solute carrier family 26, member 9 |
| TREX2 | 0.294 | 1.04E-05 | three prime repair exonuclease 2 |
| MX2 | 0.317 | 0.00491 | myxovirus (influenza virus) resistance 2 (mouse) |
| PAPL | 0.197 | 0.000138 | iron/zinc purple acid phosphatase-like protein |
| USP18 | 0.364 | 0.000984 | ubiquitin specific peptidase 18 |
| FAM43A | 0.382 | 4.01E-05 | family with sequence similarity 43, member A |
| IRF7 | 0.272 | 3.53E-05 | interferon regulatory factor 7 |
| IFIT1 | 0.211 | 0.003096 | interferon-induced protein with tetratricopeptide repeats 1 |
| LCE3E | 0.134 | 0.001434 | late cornified envelope 3E |
| ISG15 | 0.124 | 0.000226 | ISG15 ubiquitin-like modifier |
| C10orf99 | 0.279 | 0.000848 | chromosome 10 open reading frame 99 |
| RNF222 | 0.439 | 6.77E-05 | ring finger protein 222 |
| GM2A | 0.398 | 0.000122 | GM2 ganglioside activator |
| SERPINB13 | 0.331 | 0.00069 | serpin peptidase inhibitor, clade B (ovalbumin), member 13 |
| HIST1H4I | 0.651 | 0.000158 | histone cluster 1, H4i |
| FCHSD1 | 0.387 | 0.000306 | FCH and double SH3 domains 1 |
| KLK9 | 0.219 | 0.000436 | kallikrein-related peptidase 9 |
| CCDC19 | 0.5 | 6.02E-05 | coiled-coil domain containing 19 |
| LOC729041 | 0.337 | 0.002125 | fatty acid amide hydrolase pseudogene |
| PCP4L1 | 0.449 | 0.015145 | Purkinje cell protein 4 like 1 |
| KLK9 | 0.201 | 0.008977 | kallikrein-related peptidase 9 |

Example 2: Pharmaceutical Compositions

Examples of formulations suitable for an antibody of the present invention are shown below. Antibodies used in the formulations below are for example Antibody A, Antibody B, Antibody C or Antibody D.

Formulation 1:

| Components | Concentration [mmol/L] | Concentration [g/l] | Nominal Amount [mg/vial] V = 10.0 ml |
|---|---|---|---|
| Antibody | | 10.0 | 100.0 |
| Succinic acid | 0.7 | 0.083 | 0.8 |
| Disodium succinate hexahydrate | 24.3 | 6.564 | 65.6 |
| Sodium chloride | 125 | 7.305 | 73.1 |
| Polysorbat 20 | 0.16 | 0.20 | 0.20 |
| Water for Injection | — | Ad 1 L | Ad 1 mL |

The pH of formulation 1 is typically in the range of pH 6.0 to 7.0, for example pH 6.5. This formulation is particularly suitable for intravenous administration.

Molecular weight (MW in g/mol) of used excipients: Disodium succinate hexahydrate=270.14 g/mol; Succinic acid=118.09 g/mol; Sodium chloride=58.44 g/mol.

The osmolarity of the formulation is 300+/−30 mOsmol/kg, as determined using an Osmomat 030 (Gonotec GmbH, Berlin, Germany). The density at 20° C. of the formulation is approximately 1.0089 g/cm$^3$, as determined using a measuring unit DMA 4500 (Anton Paar GmbH, Ostfildern-Scharnhausen, Germany).

Formulation 2:

| Components | Concentration [mmol/L] | Concentration [g/l] | Nominal Amount [mg/syringe] V = 1.0 ml |
|---|---|---|---|
| Antibody | 0.6 | 90.0 | 90.0 |
| Succinic acid | 0.5 | 0.059 | 0.059 |
| Disodium succinate hexahydrate | 3.9 | 1.054 | 1.054 |
| Sorbitol | 225 | 41.00 | 41.00 |
| Polysorbat 20 | 0.16 | 0.20 | 0.20 |
| Water for Injection | — | Ad 1 L | Ad 1 mL |

The pH of formulation 2 is typically in the range of pH 5.5 to 6.5, for example 5.5 to 6.1, for example the pH is 5.8. This formulation is particularly suitable for subcutaneous administration.

Molecular weight (MW in g/mol) of used excipients:
MW: Succinic acid (C$_4$H$_6$O$_4$)=118.09 g/mol
MW: Disodium succinate hexahydrate (C$_4$O$_4$Na$_2$H$_4$×6H$_2$O)=270.14 g/mol
MW: Sorbitol=182.17 g/mol
MW: Polysorbate 20=1227.72 g/mol The osmolarity of the formulation is 300+/−30 mOsmol/kg, as determined using an Osmomat 030 (Gonotec GmbH, Berlin, Germany). The density at 20° C. of the formulation is approximately 1.040 g/cm$^3$, as determined using a measuring unit DMA 4500 (Anton Paar GmbH, Ostfildern-Scharnhausen, Germany).

Formulation 3:

| Components | Concentration [mmol/L] | Concentration [g/l] | Nominal Amount [mg/syringe] V = 1.0 ml |
|---|---|---|---|
| Antibody | 0.6 | 90.0 | 90.0 |
| Sorbitol | 240 | 43.733 | 43.733 |
| Polysorbat 20 | 0.16 | 0.20 | 0.20 |
| Water for Injection | — | Ad 1 L | Ad 1 mL |

The pH of formulation 3 is typically in the range of pH 5.5 to 6.5, for example 5.5 to 6.1, for example the pH is 5.8. This formulation is particularly suitable for subcutaneous administration.

Molecular weight (MW in g/mol) of used excipients:
MW: Sorbitol=182.17 g/mol
MW: Polysorbate 20=1227.72 g/mol.

The osmolarity of the formulation is 300+/−30 mOsmol/kg, as determined using an Osmomat 030 (Gonotec GmbH, Berlin, Germany).

The invention claimed is:

1. A method for detecting the presence or absence of a response in a patient after administration of an anti-IL-23A antibody comprising a light chain comprising the amino acid sequence of SEQ ID NO: 18 and a heavy chain comprising the amino acid sequence of SEQ ID NO: 19, comprising:
  a) obtaining a biological sample from the patient;
  b) measuring in said sample the level of one or more biomarkers, or the level of expression of one or more biomarkers;
  c) comparing the level to control value of the level of the one or more biomarkers; and
  d) determining whether or not the difference in levels between the sample and the control reflects a response in the patient,
wherein the one or more biomarkers comprises β-defensin 2.

2. The method of claim 1, wherein the level of the gene or the protein of said one or more biomarkers is measured.

3. The method of claim 1, wherein the patient suffers from psoriasis.

4. The method of claim 1, wherein the control value is calculated using samples from subjects that do not suffer from psoriasis.

5. The method of claim 1, wherein the control value is determined using samples from known psoriasis patients.

6. The method of claim 1, wherein the control value is determined using at least one previous sample taken from the patient.

7. The method of claim 1, wherein the biological sample is a skin biopsy, blood, plasma or serum sample.

8. The method claim 1, wherein the levels of biomarkers are determined by RNA sequencing or ELISA.

9. The method of claim 1, wherein the one or more biomarkers further comprises S-100A7 or neutrophil gelatinase lipocalin.

10. The method of claim 1, wherein the one or more biomarkers further comprises S-100A7 and neutrophil gelatinase lipocalin.

* * * * *